US012767930B2

(12) United States Patent
Ko

(10) Patent No.: US 12,767,930 B2
(45) Date of Patent: Oct. 20, 2026

(54) METHOD FOR PROMOTING DIFFERENTIATION OF PLURIPOTENT STEM CELLS BY REDUCING UNDIFFERENTIATED STATE THEREOF

(71) Applicant: KEIO UNIVERSITY, Tokyo (JP)

(72) Inventor: Minoru Ko, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 253 days.

(21) Appl. No.: 18/787,081

(22) Filed: Jul. 29, 2024

(65) Prior Publication Data

US 2024/0384234 A1 Nov. 21, 2024

Related U.S. Application Data

(63) Continuation of application No. 17/844,757, filed on Jun. 21, 2022, now Pat. No. 12,098,389, which is a continuation of application No. 16/072,610, filed as application No. PCT/JP2017/003325 on Jan. 31, 2017, now Pat. No. 11,396,644.

(30) Foreign Application Priority Data

Jan. 31, 2016 (JP) ................................ 2016-016785

(51) Int. Cl.

| | |
|---|---|
| ***C12N 5/071*** | (2010.01) |
| ***C12N 5/077*** | (2010.01) |
| ***C12N 5/0793*** | (2010.01) |
| ***C12N 15/09*** | (2006.01) |
| ***C12N 15/113*** | (2010.01) |

(52) U.S. Cl.

CPC ......... *C12N 5/0658* (2013.01); *C12N 5/0619* (2013.01); *C12N 5/067* (2013.01); *C12N 15/09* (2013.01); *C12N 15/113* (2013.01); *C12N 2310/14* (2013.01); *C12N 2506/02* (2013.01)

(58) Field of Classification Search

CPC .................. C12N 5/067; C12N 15/113; C12N 2310/14; C12N 5/0606; C12N 5/0696

See application file for complete search history.

(56) References Cited

U.S. PATENT DOCUMENTS

| | | | | |
|---|---|---|---|---|
| 9,574,179 | B2 * | 2/2017 | Sun ...................... | C12N 5/0619 |
| 11,396,644 | B2 | 7/2022 | Ko | |
| 2014/0370537 | A1 | 12/2014 | Sakurai et al. | |
| 2018/0072988 | A1 | 3/2018 | Sun et al. | |
| 2019/0048320 | A1 | 2/2019 | Ko | |
| 2022/0364058 | A1 | 11/2022 | Ko | |

FOREIGN PATENT DOCUMENTS

| | | |
|---|---|---|
| JP | 2004-236607 A | 8/2004 |

OTHER PUBLICATIONS

International Search Report issued in corresponding International Patent Application No. PCT/JP2017/003325 dated May 9, 2017 (6 pages).

Barberi et al., "Derivation of engraftable skeletal myoblasts from human embryonic stem cells," Nature Medicine, 2007, pp. 642-648, vol. 13, No. 5.

Bi et al., "Sox9 is required for cartilage formation," Nature Genetics, 1999, pp. 85-89, vol. 22.

Correa-Cerro et al., "Generation of mouse ES cell lines engineered for the forced induction of transcription factors," Scientific Reports, 2011, pp. 1-6, vol. 1, No. 167.

Darabi et al., "Human ES- and iPS-Derived Myogenic Progenitors Restore Dystrophin and Improve Contractility upon Transplantation in Dystrophic Mice," Cell Stem Cell, 2012, pp. 610-619, vol. 10, No. 5.

Fisher et al., "Normal Myeloid Development Requires Both the Glutamine-Rich Transactivation Domain and the PEST Region of Transcription Factor PU.1 but Not the Potent Acidic Transactivation Domain," Molecular and Cellular Biology, 1998, pp. 4347-4357, vol. 18, No. 7.

Goudenege et al., "Myoblasts Derived From Normal hESCs and Dystrophic hiPSCs Efficiently Fuse With Existing Muscle Fibers Following Transplantation," Molecular Therapy, 2012, pp. 2153-2167, vol. 20, No. 11.

Hamada et al., "Introduction of the MASH1 gene into mouse embryonic stem cells leads to differentiation of motoneuron precursors lacking Nogo receptor expression that can be applicable for transplantation to spinal cord injury," Neurobiology of Disease, 2006, pp. 509-522, vol. 22.

Ikeda et al., "Transplantation of motoneurons dervied from MASH1-transfected mouse ES cells reconstitutes neural networks and improves motor function in hemiplegic mice," Experimental Neurology, 2004, pp. 280-292, vol. 189.

Ivanova et al., "Dissecting self-renewal in stem cells with RNA interference," Nature, 2006, pp. 533-538, vol. 442.

Lee et al., "Oct-4 controls cell-cycle progression of embryonic stem cells," Biochemical Journal, 2010, pp. 171-181, vol. 426, No. 2.

Liu et al., "Epigenetic silencing of HDAC1 by miR-449a upregulates Runx2 and promotes osteoblast differentiation," International Journal of Molecular Medicine, 2015, pp. 238-246, vol. 35, No. 1.

(Continued)

*Primary Examiner* — Valarie E Bertoglio

(74) *Attorney, Agent, or Firm* — Kilyk & Bowersox, P.L.L.C.

(57) ABSTRACT

In related-art methods of differentiating pluripotent stem cells into a desired cell type, there has not been established a differentiation induction method using human ES/iPS cells and being highly efficient. Many attempts have been made, including a stepwise differentiation induction method based on the control of culture conditions or the addition of, for example, various cell growth factors/differentiation factors to a culture solution, but the use of complicated culture steps is a big problem. A method of inducing differentiation into a desired cell type within a short period of time and with high efficiency by use of a pluripotent stem cell that actively undergoes cell differentiation, which is obtained by reducing an undifferentiated state of the pluripotent stem cell, has been developed, and thus the present invention has been completed.

2 Claims, 9 Drawing Sheets

Specification includes a Sequence Listing.

(56) References Cited

OTHER PUBLICATIONS

Livigni et al., "A Conserved Oct4/POUV-Dependent Network Links Adhesion and Migration to Progenitor Maintenance," Current Biology, 2013, pp. 2233-2244, vol. 23.
Nishiyama et al., "Uncovering Early Response of Gene Regulatory Networks in ESCs by Systematic Induction of Transcription Factors," Cell Stem Cell, 2009, pp. 420-433, vol. 5.
Niwa et al., "Quantitative expression of Oct-3/4 defines differentiation, dedifferentiation of self-renewal of ES cells," Nature Genetics, 2000, pp. 372-376, vol. 24, No. 4.
Sharov et al., "Identification of Pou5fl, Sox2, and Nanog downstream target genes with statistical confidence by applying a novel algorithm to time course microarray and genome-wide chromatin immunoprecipitation data," BMC Genomics, 2008, pp. 1-19, vol. 9, No. 269.
Sakurai, "Modeling muscular diseases using patient-derived iPS cells," Journal of Pharmaceutical Science, 2015, p. S37, vol. 128.
Tanaka et al., "Efficient and Reproducible Myogenic Differentiation from Human iPS Cells: Prospects for Modeling Miyoshi Myopathy In Vitro," PLOS One, 2013, pp. 1-14, vol. 8, Issue 4, e61540.
Tashiro et al., "Efficient Adipocyte and Osteoblast Differentiation from Mouse Induced Pluripotent Stem Cells by Adenoviral Transduction," Stem Cells, 2009, pp. 1802-1811, vol. 27, No. 8.
Yamamizu et al., "Identification of Transcription Factors for Lineage-Specific ESC Differentiation," Stem Cell Reports, 2013, pp. 1-15, vol. 1.
Ying et al., "Oct4 Coordinates with WNT Signaling to Pre-pattern Chromatin at the SOX17 Locus during Human ES Cell Differentiation into Definitive Endoderm," Stem Cell Reports, 2015, pp. 490-498, vol. 5, No. 4.
Takayama, "Establishment of a Method of Hepatocyte Differentiation from Human Pluripotent Stem Cells for Innovation Drug Development," Journal of the Pharmaceutical Society of Japan, 2015, pp. 1141-1146, vol. 135, No. 10 (machine translation of Abstract only attached).
Zhao et al., "Parallel Expression of Sox9 and Col2a1 in Cells Undergoing Chondrogenesis," Developmental Dynamics, 1997, pp. 377-386, vol. 209.
Cao, H3k27ME3 demethylases JMJD3 and/or UTX contribute to activating expression of endoderm and early lung development transcription factors FOXA2 and GATA6, American Journal of Respiratory and Critical Care Medicine, 2012, vol. 185, Supp. MeetingAbstracts, Abstract No. A3483 (abstract only).
Takayama et al., "Generation of metabolically functioning hepatocytes from human pluripotent stem cells by FOXA2 and HNF1-alpha transduction", Journal of Hepatology, 2012, vol. 57, pp. 628-636.
Extended European Search Report issued in corresponding European Patent Application No. 17744467.6 dated Jul. 3, 2019 (8 pages).
Hough et al., "Differentiation of Mouse Embryonic Stem Cells after RNA Interference-Mediated Silencing of OCT4 and Nanog," XP-002791960, Stem Cells, 2006, vol. 24, pp. 1467-1475.
Zhang et al., "Oct4 Maintains the Pluripotency of Human Embryonic Stem Cells by Inactivating p53 Through Sirt1-Mediated Deacetylation," XP-002791961, Stem Cells, 2014, vol. 32, pp. 157-165.
Nishiyama et al., "Systematic repression of transcription factors reveals limited patterns of gene expression changes in ES cells," XP-002791962, Scientific Reports, 2013, vol. 3, No. 1390, pp. 1-6.
Kushwaha et al., "Interrogation of a Context-Specific Transcription Factor Network Identifies Novel Regulators of Pluripotency," XP-002791963, Stem Cells, 2015, vol. 33, pp. 367-377.
Zhou et al., "Generation of Induced Pluripotent Stem Cells Using Recombinant Proteins," Cell Stem Cell 4, May 8, 2009, pp. 381-384.
Kodaka et al., "Skeletal Muscle Cell Induction from Pluripotent Stem Cells," Stem Cells International, 2017, Article ID 1376151, pp. 1-16.
Warren et al., "Highly Efficient Reprogramming to Pluripotency and Directed Differentiation of Human Cells with Synthetic Modified mRNA," Cell Stem Cell 7, Nov. 5, 2010, pp. 618-630.
Takada et al., "Efficient gene silencing and cell differentiation using siRNA in mouse and monkey ES cells," Biochemical and Biophysical Research Communications 331, 2005, pp. 1039-1044.

* cited by examiner

METHOD FOR PROMOTING DIFFERENTIATION OF PLURIPOTENT STEM CELLS BY REDUCING UNDIFFERENTIATED STATE THEREOF

TECHNICAL FIELD

The present application is a continuation of U.S. patent application Ser. No. 17/844,757, filed Jun. 21, 2022, which in turn is a continuation of U.S. patent application Ser. No. 16/072,610 filed Jul. 25, 2018 which is a National Stage Application of PCT/JP2017/003325, filed Jan. 31, 2017, which claims priority from Japanese Patent Application No. 2016-016785, which is incorporated herein by reference. The present invention relates to a method of reducing an undifferentiated state of a pluripotent stem cell, and more specifically, to a method of differentiating a pluripotent stem cell into a desired cell type with high efficiency and a differentiation induction kit to be used for the differentiation method.

REFERENCE TO AN ELECTRONIC SEQUENCE LISTING

The contents of the electronic sequence listing (3190-231-02-Sequence-Listing.xml; Size: 81,855 bytes; and Date of Creation: Jul. 29, 2024) is herein incorporated by reference in its entirety.

BACKGROUND ART (on Induction of Differentiation of Pluripotent Stem Cells)

Regenerative medicine using cells obtained by inducing differentiation of pluripotent stem cells, such as embryonic stem cells (ES cells) or induced pluripotent stem cells (iPS cells) is a therapeutic method for which all peoples of the world have high expectations and which are desired to be realized soon. As regenerative medicine, a transplantation therapy with retinal pigment epithelial cells derived from iPS cells is fresh in our memory. However, a technology for rapidly generating mature differentiated cells suited for cell transplantation in a sufficient amount is still under development and has much room for development.

A current mainstream method of inducing differentiation of pluripotent stem cells into a desired cell type is a method involving sequentially adding cytokines/growth factors suited for respective differentiation stages to a medium to cause differentiation via an embryoid body and progenitor cells. This method has problems in, for example, that a culture period until differentiated cells of interest are obtained is long, that differentiation induction efficiency is not high, and that cells of different cell lineages are mixed with each other.

In recent years, attempts have been actively made to direct cell differentiation by forcibly expressing, in ES/iPS cells, one or a combination of a plurality of tissue-specifically expressed transcription factors. This differentiation induction method using transcription factors can directly induce ES/iPS cells into differentiated cells of interest, and hence is expected to be extremely effective means. However, even with this technique, differentiation induction efficiency for some cell types is still low, and thus, it is difficult to obtain a sufficient number of differentiated cells required for regenerative medicine.

In view of the foregoing, there has been a demand for development of a novel differentiation induction method for producing differentiated cells of interest from pluripotent stem cells more rapidly and more uniformly with higher efficiency.

(Current Situation of Induction of Differentiation of Pluripotent Stem Cells in Related Art)

Non Patent Literatures 1 to 4, which are related art, are each directed to a system for facilitating induction of differentiation of ES/iPS cells. For an example, there was a disclosure that ES/iPS cells were induced into skeletal muscle differentiation.

However, those differentiation induction methods are clearly different from a differentiation induction method of the present invention.

In Non Patent Literature 5, there was a disclosure that "in research using mouse ES cells, when expression of a transcription factor Oct3/4 is repressed, trophectoderm can be derived from the ES cells." In addition, in Patent Literature 1, there was a disclosure that "differentiation of neural stem cells into neurons, glial cells, and the like can be regulated by controlling an expression amount of an Oct-3/4 protein in the neural stem cells."

However, there was no disclosure or suggestion of a method of efficiently inducing differentiation into a desired cell type by introducing a transcription factor required for induction of differentiation into the desired cell type into a pluripotent stem cell.

CITATION LIST

Patent Literature

[PTL 1] JP 2004-236607 A

Non Patent Literature

[NPL 1] Nature medicine 13:642-648.
[NPL 2] Cell stem cell 10:610-619.
[NPL 3] Mol Ther. November; 20 (11): 2153-67.
[NPL 4] PLOS One. 2013 Apr. 23; 8 (4): e61540.
[NPL 5] Nat. Genet. 24 (4): 372-6.

SUMMARY OF INVENTION

Technical Problem

In related-art methods of differentiating pluripotent stem cells into a desired cell type, there has not been established a differentiation induction method using human ES/iPS cells and being stable and highly efficient. Many attempts have been made, including a stepwise differentiation induction method based on the control of culture conditions or the addition of, for example, various cell growth factors/differentiation factors to a culture solution, but the use of complicated culture steps is a big problem. In addition, there are also big problems in, for example, that the speed of cell differentiation is low, and hence long-period culture is required, and that the differentiation efficiency is low, and hence it is difficult to obtain a sufficient number of required cells.

Solution to Problem

The inventors of the present invention have presumed that the above-mentioned problems are partly due to the fact that pluripotent stem cells have a property of maintaining the undifferentiated state of the cells by various mechanisms. In view of this, the inventors have developed a method of inducing differentiation into a desired cell type within a short period of time and with high efficiency by reducing undifferentiated state maintenance of a pluripotent stem cell to generate a pluripotent stem cell that actively proceeds to a differentiated cell type.

Further, the inventors have developed a method of more potently inducing differentiation into a desired cell type within a short period of time and with high efficiency by not only reducing undifferentiated state maintenance of a pluripotent stem cell but also reducing differentiation resistance thereof.

Thus, the present invention has been completed.

That is, the present invention includes the following.

1. A differentiation induction kit for differentiating a pluripotent stem cell into a desired cell type, including at least any one of the following items (1) to (8):

(1) a pluripotent stem cell and a gene for a compound having an action of substantially removing or reducing an expression amount of a POU5F1 protein;

(2) a pluripotent stem cell in which an expression amount of a POU5F1 protein has been substantially removed or reduced;

(3) a pluripotent stem cell in which a gene for a compound having an action of substantially removing or reducing an expression amount of a POU5F1 protein is forcibly expressed;

(4) a gene construct carrying a gene for a compound having an action of substantially removing or reducing an expression amount of a POU5F1 protein, and a pluripotent stem cell;

(5) a pluripotent stem cell having a gene construct carrying a gene for a compound having an action of substantially removing or reducing an expression amount of a POU5F1 protein inserted into a genome thereof;

(6) a pluripotent stem cell in which a POU5F1 gene has been disrupted;

(7) a pluripotent stem cell in which an expression amount of a POU5F1 protein has been substantially removed or reduced and which has a histone in which H3K27me3 modification has been substantially removed or reduced; and (8) a pluripotent stem cell, and a gene for a compound having an action of substantially removing or reducing an expression amount of a POU5F1 protein and a demethylase gene.

2. A differentiation induction kit according to the above-mentioned item 1, wherein the gene for the compound having an action of substantially removing or reducing an expression amount of a POU5F1 protein includes a gene expressing siRNA of POU5F1, a gene expressing shRNA of POU5F1, a gene expressing an antisense strand of POU5F1, and/or a gene for an antibody against POU5F1.

3. A differentiation induction kit according to the above-mentioned item 1 or 2, further including a transcription factor required for induction of differentiation into the desired cell type.

4. A differentiation induction kit according to the above-mentioned item 3, wherein a transcription factor gene for the transcription factor is carried on a Sendai virus vector.

5. A differentiation induction kit for differentiating a pluripotent stem cell into a skeletal muscle cell, including at least any one of the following items (1) to (8):

(1) a pluripotent stem cell in which an expression amount of a POU5F1 protein has been substantially removed or reduced, and a transcription factor MYOD1;

(2) a gene for a compound having an action of substantially removing or reducing an expression amount of a POU5F1 protein, a transcription factor MYOD1, and a pluripotent stem cell;

(3) a pluripotent stem cell in which a gene for a compound having an action of substantially removing or reducing an expression amount of a POU5F1 protein is forcibly expressed, and a transcription factor MYOD1;

(4) a gene construct carrying a gene for a compound having an action of substantially removing or reducing an expression amount of a POU5F1 protein, a transcription factor MYOD1, and a pluripotent stem cell;

(5) a pluripotent stem cell having a gene construct carrying a gene for a compound having an action of substantially removing or reducing an expression amount of a POU5F1 protein inserted into a genome thereof, and a transcription factor MYOD1;

(6) a pluripotent stem cell in which a POU5F1 gene has been disrupted, and a transcription factor MYOD1;

(7) a transcription factor MYOD1, and a pluripotent stem cell in which an expression amount of a POU5F1 protein has been substantially removed or reduced and which has a histone in which H3K27me3 modification has been substantially removed or reduced; and (8) a pluripotent stem cell, and a transcription factor MYOD1, a gene for a compound having an action of substantially removing or reducing an expression amount of a POU5F1 protein, and a demethylase gene.

6. A differentiation induction kit for differentiating a pluripotent stem cell into a neuron, including at least any one of the following items (1) to (8):

(1) a pluripotent stem cell in which an expression amount of a POU5F1 protein has been substantially removed or reduced, and transcription factors NEUROG1, NEUROG2, NEUROG3, NEUROD1, and NEUROD2;

(2) a gene for a compound having an action of substantially removing or reducing an expression amount of a POU5F1 protein, transcription factors NEUROG1, NEUROG2, NEUROG3, NEUROD1, and NEUROD2, and a pluripotent stem cell;

(3) a pluripotent stem cell in which a gene for a compound having an action of substantially removing or reducing an expression amount of a POU5F1 protein is forcibly expressed, and transcription factors NEUROG1, NEUROG2, NEUROG3, NEUROD1, and NEUROD2;

(4) a gene construct carrying a gene for a compound having an action of substantially removing or reducing an expression amount of a POU5F1 protein, transcription factors NEUROG1, NEUROG2, NEUROG3, NEUROD1, and NEUROD2, and a pluripotent stem cell;

(5) a pluripotent stem cell having a gene construct carrying a gene for a compound having an action of substantially removing or reducing an expression amount of a POU5F1 protein inserted into a genome thereof, and transcription factors NEUROG1, NEUROG2, NEUROG3, NEUROD1, and NEUROD2;

(6) a pluripotent stem cell in which a POU5F1 gene has been disrupted, and transcription factors NEUROG1, NEUROG2, NEUROG3, NEUROD1, and NEUROD2;

(7) transcription factors NEUROG1, NEUROG2, NEUROG3, NEUROD1, and NEUROD2, and a pluripotent stem cell in which an expression amount of a POU5F1 protein has been substantially removed or reduced and which has a histone in which H3K27me3 modification has been substantially removed or reduced; and (8) a pluripotent stem cell, and transcription factors NEUROG1, NEUROG2, NEUROG3, NEUROD1, and NEUROD2, a gene for a compound having an action of substantially removing or reducing an expression amount of a POU5F1 protein, and a demethylase gene.

7. A differentiation induction kit for differentiating a pluripotent stem cell into a hepatocyte, including at least any one of the following items (1) to (8):

(1) a pluripotent stem cell in which an expression amount of a POU5F1 protein has been substantially removed or reduced, and a transcription factor HNF1A;

(2) a gene for a compound having an action of substantially removing or reducing an expression amount of a POU5F1 protein, a transcription factor HNF1A, and a pluripotent stem cell;

(3) a pluripotent stem cell in which a gene for a compound having an action of substantially removing or reducing an expression amount of a POU5F1 protein is forcibly expressed, and a transcription factor HNF1A;

(4) a gene construct carrying a gene for a compound having an action of substantially removing or reducing an expression amount of a POU5F1 protein, a transcription factor HNF1A, and a pluripotent stem cell;

(5) a pluripotent stem cell having a gene construct carrying a gene for a compound having an action of substantially removing or reducing an expression amount of a POU5F1 protein inserted into a genome thereof, and a transcription factor HNF1A;

(6) a pluripotent stem cell in which a POU5F1 gene has been disrupted, and a transcription factor HNF1A;

(7) a transcription factor HNF1A, and a pluripotent stem cell in which an expression amount of a POU5F1 protein has been substantially removed or reduced and which has a histone in which H3K27me3 modification has been substantially removed or reduced; and (8) a pluripotent stem cell, a transcription factor HNF1A, a demethylase gene, and a gene for a compound having an action of substantially removing or reducing an expression amount of a POU5F1 protein.

8. A differentiation induction kit according to the above-mentioned item 3 or 4, wherein the differentiation induction kit is as described in any one of the following items (1) to (6):

(1) the transcription factor required for induction of differentiation into the desired cell type includes MYOD1, and the desired cell type includes a skeletal muscle cell;

(2) the transcription factor required for induction of differentiation into the desired cell type includes HNF1A, and the desired cell type includes a hepatocyte;

(3) the transcription factor required for induction of differentiation into the desired cell type includes SOX9, and the desired cell type includes a chondrocyte;

(4) the transcription factor required for induction of differentiation into the desired cell type includes RUNX2, and the desired cell type includes a bone cell;

(5) the transcription factor required for induction of differentiation into the desired cell type includes SPI1, and the desired cell type includes a hematopoietic cell; and (6) the transcription factor required for induction of differentiation into the desired cell type includes ASCL1, and the desired cell type includes a neuron.

9. A method of differentiating a pluripotent stem cell into a desired cell type, including any one of the following steps (1) to (9):

(1) a step of adding a gene for a compound having an action of substantially removing or reducing an expression amount of a POU5F1 protein, and a transcription factor required for induction of differentiation into the desired cell type to a pluripotent stem cell;

(2) a step of inserting a gene construct carrying a gene for a compound having an action of substantially removing or reducing an expression amount of a POU5F1 protein, and a transcription factor gene required for induction of differentiation into the desired cell type into a genome of a pluripotent stem cell;

(3) a step of inserting a gene construct carrying a gene for a compound having an action of substantially removing or reducing an expression amount of a POU5F1 protein, and a gene construct carrying a transcription factor required for induction of differentiation into the desired cell type into a genome of a pluripotent stem cell;

(4) a step of adding a transcription factor required for induction of differentiation into the desired cell type to a pluripotent stem cell, in which an expression amount of a POU5F1 protein has been substantially removed or reduced;

(5) a step of adding a transcription factor required for induction of differentiation into the desired cell type to a pluripotent stem cell, in which a compound having an action of substantially removing or reducing an expression amount of a POU5F1 protein is forcibly expressed;

(6) a step of adding a compound having an action of substantially removing or reducing an expression amount of a POU5F1 protein, and a transcription factor required for differentiation into the desired cell type to a pluripotent stem cell;

(7) a step of adding a transcription factor required for induction of differentiation into the desired cell type to a pluripotent stem cell, in which a POU5F1 gene has been disrupted;

(8) a step of adding a gene for a compound having an action of substantially removing or reducing an expression amount of a POU5F1 protein, a demethylase gene, and a transcription factor required for induction of differentiation into the desired cell type to a pluripotent stem cell; and (9) a step of adding a transcription factor required for induction of differentiation into the desired cell type to a pluripotent stem cell in which an expression amount of a POU5F1 protein has been substantially removed or reduced and which has a histone in which H3K27me3 modification has been substantially removed or reduced.

10. A differentiation method according to the above-mentioned item 9, wherein the gene for the compound having an action of substantially removing or reducing an expression amount of a POU5F1 protein includes a gene expressing siRNA of POU5F1, a gene expressing shRNA of POU5F1, a gene expressing an antisense strand of POU5F1, and/or a gene for an antibody against POU5F1.

11. A differentiation method according to the above-mentioned item 9 or 10, wherein a gene for the transcription factor is carried on a Sendai virus vector.

12. A method of differentiating a pluripotent stem cell into a skeletal muscle cell, including any one of the following steps (1) to (9):

(1) a step of adding a gene for a compound having an action of substantially removing or reducing an expression amount of a POU5F1 protein and a transcription factor MYOD1 to a pluripotent stem cell;

(2) a step of inserting a gene construct carrying a gene for a compound having an action of substantially removing or reducing an expression amount of a POU5F1 protein and a gene for a transcription factor MYOD1 into a genome of a pluripotent stem cell;

(3) a step of inserting a gene construct carrying a gene for a compound having an action of substantially removing or reducing an expression amount of a POU5F1 protein and a gene construct carrying a transcription factor MYOD1 into a genome of a pluripotent stem cell;

(4) a step of adding a transcription factor MYOD1 to a pluripotent stem cell in which an expression amount of a POU5F1 protein has been substantially removed or reduced;

(5) a step of adding a transcription factor MYOD1 to a pluripotent stem cell in which a compound having an action of substantially removing or reducing an expression amount of a POU5F1 protein is forcibly expressed;

(6) a step of adding a compound having an action of substantially removing or reducing an expression amount of a POU5F1 protein and a transcription factor MYOD1 to a pluripotent stem cell;

(7) a step of adding a transcription factor MYOD1 to a pluripotent stem cell in which a POU5F1 gene has been disrupted;

(8) a step of adding a gene for a compound having an action of substantially removing or reducing an expression amount of a POU5F1 protein, a demethylase gene, and a transcription factor MYOD1 to a pluripotent stem cell; and (9) a step of adding a transcription factor MYOD1 to a pluripotent stem cell in which an expression amount of a POU5F1 protein has been substantially removed or reduced and which has a histone in which H3K27me3 modification has been substantially removed or reduced.

13. A method of differentiating a pluripotent stem cell into a neuron, including any one of the following steps (1) to (9):

(1) a step of adding a gene for a compound having an action of substantially removing or reducing an expression amount of a POU5F1 protein and transcription factors NEUROG1, NEUROG2, NEUROG3, NEUROD1, and/or NEUROD2 to a pluripotent stem cell;

(2) a step of inserting a gene construct carrying a gene for a compound having an action of substantially removing or reducing an expression amount of a POU5F1 protein and genes for transcription factors NEUROG1, NEUROG2, NEUROG3, NEUROD1, and/or NEUROD2 into a genome of a pluripotent stem cell;

(3) a step of inserting a gene construct carrying a gene for a compound having an action of substantially removing or reducing an expression amount of a POU5F1 protein and a gene construct carrying transcription factors NEUROG1, NEUROG2, NEUROG3, NEUROD1, and/or NEUROD2 into a genome of a pluripotent stem cell;

(4) a step of adding transcription factors NEUROG1, NEUROG2, NEUROG3, NEUROD1, and/or NEUROD2 to a pluripotent stem cell in which an expression amount of a POU5F1 protein has been substantially removed or reduced;

(5) a step of adding transcription factors NEUROG1, NEUROG2, NEUROG3, NEUROD1, and/or NEUROD2 to a pluripotent stem cell in which a compound having an action of substantially removing or reducing an expression amount of a POU5F1 protein is forcibly expressed;

(6) a step of adding a compound having an action of substantially removing or reducing an expression amount of a POU5F1 protein and transcription factors NEUROG1, NEUROG2, NEUROG3, NEUROD1, and/or NEUROD2 to a pluripotent stem cell;

(7) a step of adding transcription factors NEUROG1, NEUROG2, NEUROG3, NEUROD1, and/or NEUROD2 to a pluripotent stem cell in which a POU5F1 gene has been disrupted;

(8) a step of adding a gene for a compound having an action of substantially removing or reducing an expression amount of a POU5F1 protein, a demethylase gene, and transcription factors NEUROG1, NEUROG2, NEUROG3, NEUROD1, and/or NEUROD2 to a pluripotent stem cell; and (9) a step of adding transcription factors NEUROG1, NEUROG2, NEUROG3, NEUROD1, and/or NEUROD2 to a pluripotent stem cell in which an expression amount of a POU5F1 protein has been substantially removed or reduced and which has a histone in which H3K27me3 modification has been substantially removed or reduced.

14. A method of differentiating a pluripotent stem cell into a hepatocyte, including any one of the following steps (1) to (9):

(1) a step of adding a gene for a compound having an action of substantially removing or reducing an expression amount of a POU5F1 protein and a transcription factor HNF1A to a pluripotent stem cell;

(2) a step of inserting a gene construct carrying a gene for a compound having an action of substantially removing or reducing an expression amount of a POU5F1 protein and a gene for a transcription factor HNF1A into a genome of a pluripotent stem cell;

(3) a step of inserting a gene construct carrying a gene for a compound having an action of substantially removing or reducing an expression amount of a POU5F1 protein and a gene construct carrying a transcription factor HNF1A into a genome of a pluripotent stem cell;

(4) a step of adding a transcription factor HNF1A to a pluripotent stem cell in which an expression amount of a POU5F1 protein has been substantially removed or reduced;

(5) a step of adding a transcription factor HNF1A to a pluripotent stem cell in which a compound having an action of substantially removing or reducing an expression amount of a POU5F1 protein is forcibly expressed;

(6) a step of adding a compound having an action of substantially removing or reducing an expression amount of a POU5F1 protein and a transcription factor HNF1A to a pluripotent stem cell;

(7) a step of adding a transcription factor HNF1A to a pluripotent stem cell in which a POU5F1 gene has been disrupted;

(8) a step of adding a gene for a compound having an action of substantially removing or reducing an expression amount of a POU5F1 protein, a demethylase gene, and a transcription factor HNF1A to a pluripotent stem cell; and (9) a step of adding a transcription factor HNF1A to a pluripotent stem cell in which an expression amount of a POU5F1 protein has been substantially removed or reduced and which has a histone in which H3K27me3 modification has been substantially removed or reduced.

15. A differentiation method according to any one of the above-mentioned items 9 to 11, wherein the differentiation method is as described in any one of the following items (1) to (6):

(1) the transcription factor required for induction of differentiation into the desired cell type includes MYOD1, and the desired cell type includes a skeletal muscle cell;
(2) the transcription factor required for induction of differentiation into the desired cell type includes HNF1A, and the desired cell type includes a hepatocyte;
(3) the transcription factor required for induction of differentiation into the desired cell type includes SOX9, and the desired cell type includes a chondrocyte;
(4) the transcription factor required for induction of differentiation into the desired cell type includes RUNX2, and the desired cell type includes a bone cell;
(5) the transcription factor required for induction of differentiation into the desired cell type includes SPI1, and the desired cell type includes a hematopoietic cell; and
(6) the transcription factor required for induction of differentiation into the desired cell type includes ASCL1, and the desired cell type includes a neuron.

Advantageous Effects of Invention

The method of differentiating a pluripotent stem cell into a desired cell type with high efficiency and differentiation induction kit for differentiating a pluripotent stem cell into a desired cell type with high efficiency of the present invention each have at least any one or more of the following effects.

(1) The period of time required for cell differentiation starting with the pluripotent stem cell is shortened and the differentiation induction efficiency is improved.
(2) As modified synthetic mRNA for a gene is used to introduce the gene into the pluripotent stem cell, the introduced gene is not incorporated into the genome of the pluripotent stem cell, and the result is that there is no risk of canceration or the like after cell differentiation induction.
(3) In the introduction of the gene into the pluripotent stem cell using the modified synthetic mRNA, the timing and number of times of the addition of the mRNA for the gene can be easily changed, and hence optimal conditions specific to each of cell types can be selected.
(4) A method of reducing undifferentiated state maintenance of a pluripotent stem cell and a method of reducing differentiation resistance thereof are combined with each other to shorten the period of time required for cell differentiation starting with the pluripotent stem cell and improve the differentiation induction efficiency in a synergistic manner.

DESCRIPTION OF EMBODIMENTS

A method of reducing an undifferentiated state of a pluripotent stem cell of the present invention (hereinafter sometimes referred to as "method of the present invention") is described below, though the method is not particularly limited as long as the method is a method capable of reducing undifferentiated state maintenance of a pluripotent stem cell, and further, is a method capable of not only reducing undifferentiated state maintenance of a pluripotent stem cell but also reducing differentiation resistance thereof as required.

(Pluripotent Stem Cell)

The pluripotent stem cell to be used in the method of the present invention is not particularly limited, but is preferably derived from a mammal, particularly preferably derived from a human. The pluripotent stem cell is, for example, a human ES cell, a human iPS cell, or any combination thereof, is not particularly limited, and encompasses tissue stem cells derived from tissues and organs, dermal fibroblasts, and all kinds of cells derived from tissues or organs.

(Reducing Undifferentiated State Maintenance of Pluripotent Stem Cell)

Figure 1:
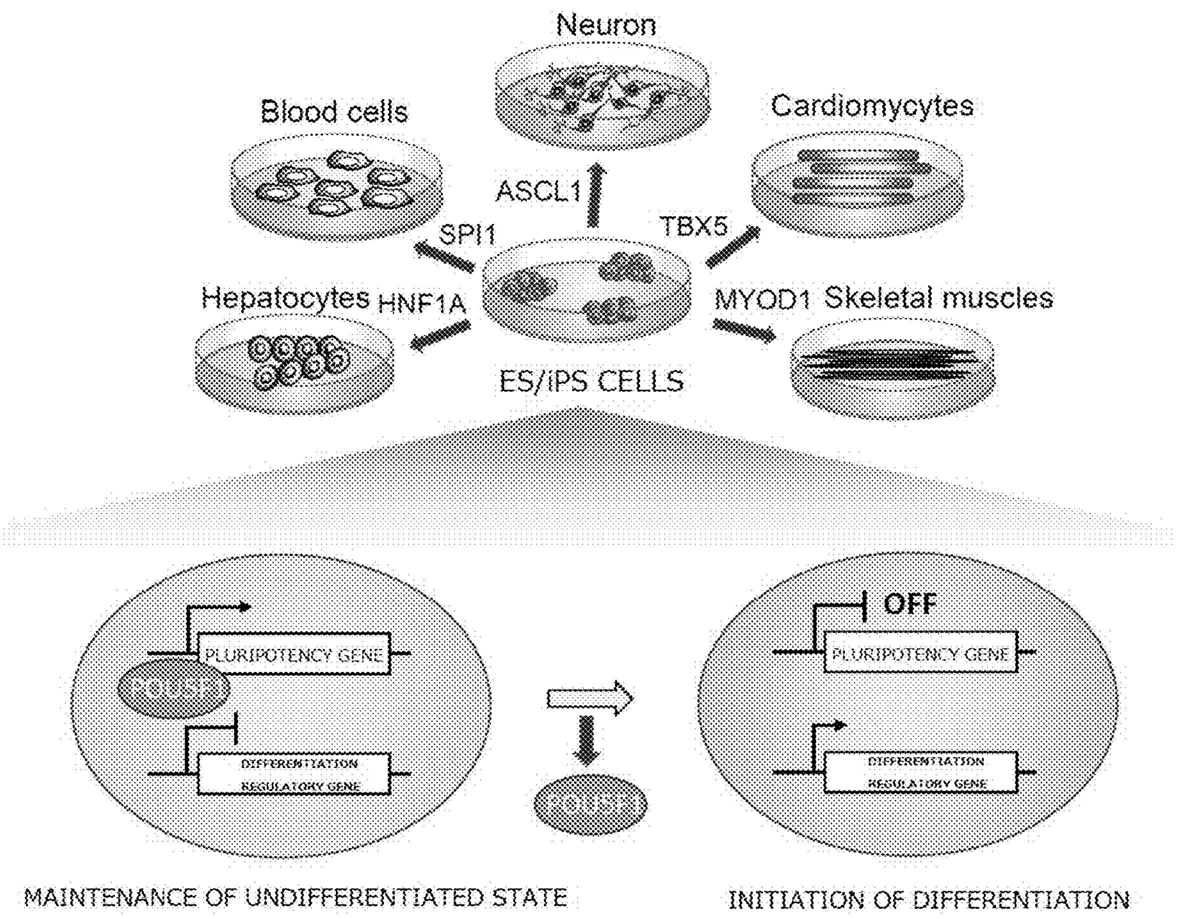
FIG. 1 A schematic diagram of a method of inducing differentiation of a pluripotent stem cell in which an expression amount of a POU5F1 protein has been reduced of the present invention. It is illustrated that differentiation into desired cells can be induced by introducing (adding) modified synthetic RNAs for tissue-specific transcription factors to pluripotent stem cells in which the function of POU5F1, a gene responsible for an undifferentiated state, has been suppressed by an RNA interference method.
Figure 2A:
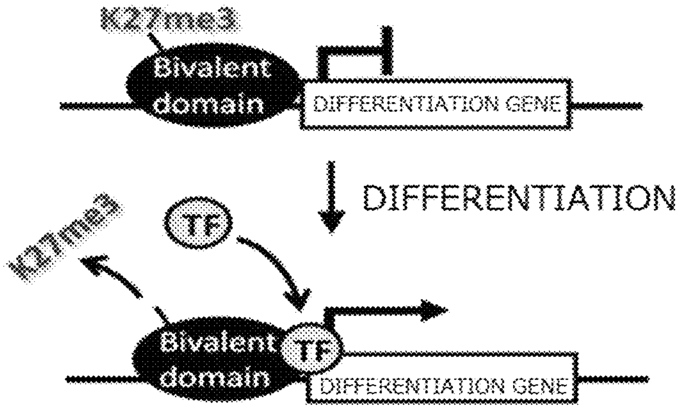
FIG. 2A A schematic diagram of a method of reducing differentiation resistance of a pluripotent stem cell to a desired cell type of the present invention.
Figure 2B:
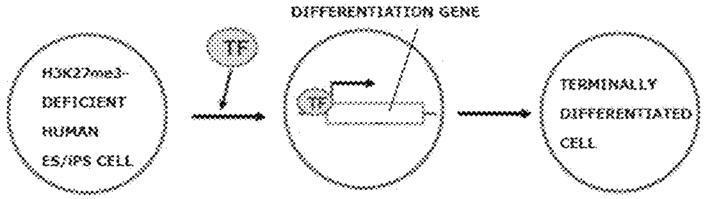
FIG. 2B When H3K27me3 modification in a human ES or iPS cell is reduced or removed, a transcription factor (TF) binds to the promoter site of a downstream gene to enhance the expression of a group of development/differentiation-related genes, resulting in differentiation.
Figure 2C:
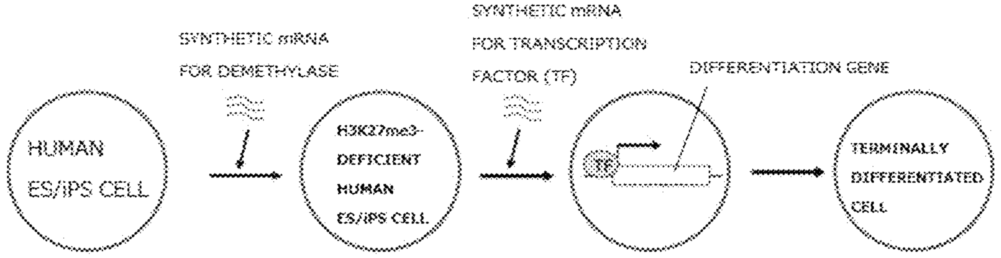
FIG. 2C A method of inducing differentiation of a human ES cell or iPS cell by introducing modified synthetic mRNA for a demethylase, and then introducing modified synthetic mRNA for the transcription factor (TF).
Figure 2D:
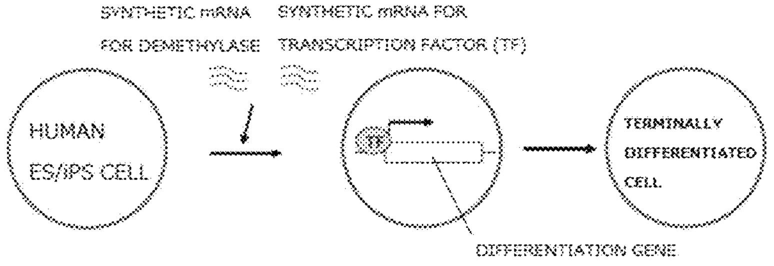
FIG. 2D A method of inducing differentiation of a human ES cell or iPS cell by simultaneously introducing the modified synthetic mRNAs for the demethylase and the transcription factor (TF).

In pluripotent stem cells, the expression of a transcription factor POU5F1 (SEQ ID NOS: 1 and 2: POU domain, 5, transcription class factor 1 isoform 1: http://www.ncbi.nlm-.nih.gov/protein/NP_002692, other names: OCT3, OCT4, OTF3, OTF4, OTF-3, Oct-3, Oct-4, MGC22487) is essential to the undifferentiated state maintenance of the pluripotent stem cells. POU5F1 is specifically expressed in pluripotent cells, such as reproductive cells and a preimplantation early embryo. In Examples of the present invention, it has been confirmed that differentiation into a desired cell type can be efficiently induced by introducing a transcription factor required for induction of differentiation into the desired cell type into a pluripotent stem cell in which an expression amount of a POU5F1 protein has been reduced (see FIG. 1). That is, the "reducing undifferentiated state maintenance of a pluripotent stem cell" of the present invention means substantially removing or reducing an expression amount of a POU5F1 protein in the pluripotent stem cell. The substantially removing or reducing an expression amount of a POU5F1 protein encompasses inhibiting the process of any one of the transcription and translation stages of POU5F1 and/or inhibiting the activity of the translated POU5F1 protein, and is not particularly limited.

In addition, a state in which the expression amount of the POU5F1 protein in the pluripotent stem cell has been substantially removed or reduced may be confirmed by a comparison to the degree of the expression amount of the POU5F1 protein (or expression amount of the POU5F1 gene) in a pluripotent stem cell that has not been subjected to the removing or the reducing. For example, the state (degree) in which the expression amount of the POU5F1 protein in the pluripotent stem cell has been substantially removed or reduced is from 95 to 1, from 90 to 2, from 85 to 3, from 80 to 4, from 75 to 5, from 70 to 6, from 65 to 7, from 60 to 8, from 50 to 10, from 40 to 15, from 30 to 20, or about 25 when compared to the expression amount of the POU5F1 protein in the pluripotent stem cell that has not been removed or reduced, which is defined as 100. The degree of the expression amount of the POU5F1 protein in the pluripotent stem cell may be easily measured by using a commercially available anti-POU5F1 antibody, and the gene expression amount of POU5F1 may be measured by a method known per se.

(Reducing Differentiation Resistance of Pluripotent Stem Cell to Desired Cell Type)

In pluripotent stem cells, a special chromatin structure called a "bivalent domain" is formed in each promoter region of a group of genes involved in differentiation, and under a stemness-maintaining state, the group of genes involved in development/differentiation are in a standby state so as not to be easily expressed. The inventors of the present invention have confirmed that "as a methyl group modification of a histone called H3K27me3 is removed or reduced in the "bivalent domain", the expression of differentiation genes required for induction of differentiation into the desired cell type is rapidly and efficiently facilitated" (see FIGS. 2A-2D).

Namely, the "reducing differentiation resistance of a pluripotent stem cell to a desired cell type" of the present invention means that the H3K27me3 modification of the pluripotent stem cell is substantially removed or reduced.

In addition, a state in which the H3K27me3 modification of the pluripotent stem cell has been substantially removed or reduced may be confirmed by a comparison to the degree of the H3K27me3 modification of a pluripotent stem cell that has not been subjected to the removing or the reducing. For example, the state (degree) in which the H3K27me3 modification of the pluripotent stem cell has been substantially removed or reduced is from 95 to 1, from 90 to 2, from 85 to 3, from 80 to 4, from 75 to 5, from 70 to 6, from 65 to 7, from 60 to 8, from 50 to 10, from 40 to 20, or about 30 when compared to the degree of the H3K27me3 modification of the pluripotent stem cell that has not been removed or reduced, which is defined as 100. The degree of the H3K27me3 modification of the pluripotent stem cell may be easily measured by using a commercially available anti-Histone H3K27me3 antibody, and the gene expression amount of H3K27me3 may be measured by a method known per se.

(Method of Inducing Differentiation of Pluripotent Stem Cell into Desired Cell Type with High Efficiency of the Present Invention)

As described above, the method of the present invention is not particularly limited as long as the method is a method of reducing undifferentiated state maintenance of a pluripotent stem cell, and further, is a method capable of reducing differentiation resistance of a pluripotent stem cell to the desired cell type as required, and may be exemplified by the following.

(Use of Modified Synthetic mRNA for Target Gene)

The method of the present invention includes adding (introducing, transfecting), to a pluripotent stem cell, a gene for a compound having an action of substantially removing or reducing an expression amount of a POU5F1 protein (gene expressing small interfering RNA (siRNA) against POU5F1, gene expressing shRNA against POU5F1, gene expressing an antisense strand of POU5F1, or antibody gene), and further, a gene for a transcription factor required for induction of differentiation into the desired cell type.

Similarly, the method of the present invention includes adding (introducing, transfecting), to a pluripotent stem cell, a gene for a compound having an action of substantially removing or reducing H3K27me3 modification as required, and further, a gene for a transcription factor required for induction of differentiation of the pluripotent stem cell into the desired cell type.

The term "gene" as used herein encompasses not only double-stranded nucleic acids, but also their respective constituent single strands, such as plus strands (or sense strands) or complementary strands (or antisense strands), linear nucleic acids, and circular nucleic acids, and encompasses DNA, RNA, mRNA, cDNA, and the like, unless otherwise stated.

In addition, the term "target gene" is meant to encompass both of: the gene for the compound having an action of substantially removing or reducing an expression amount of a POU5F1 protein and/or the gene for the compound having an action of substantially removing or reducing H3K27me3 modification; and the transcription factor required for induction of differentiation into the desired cell type.

Figure 3:
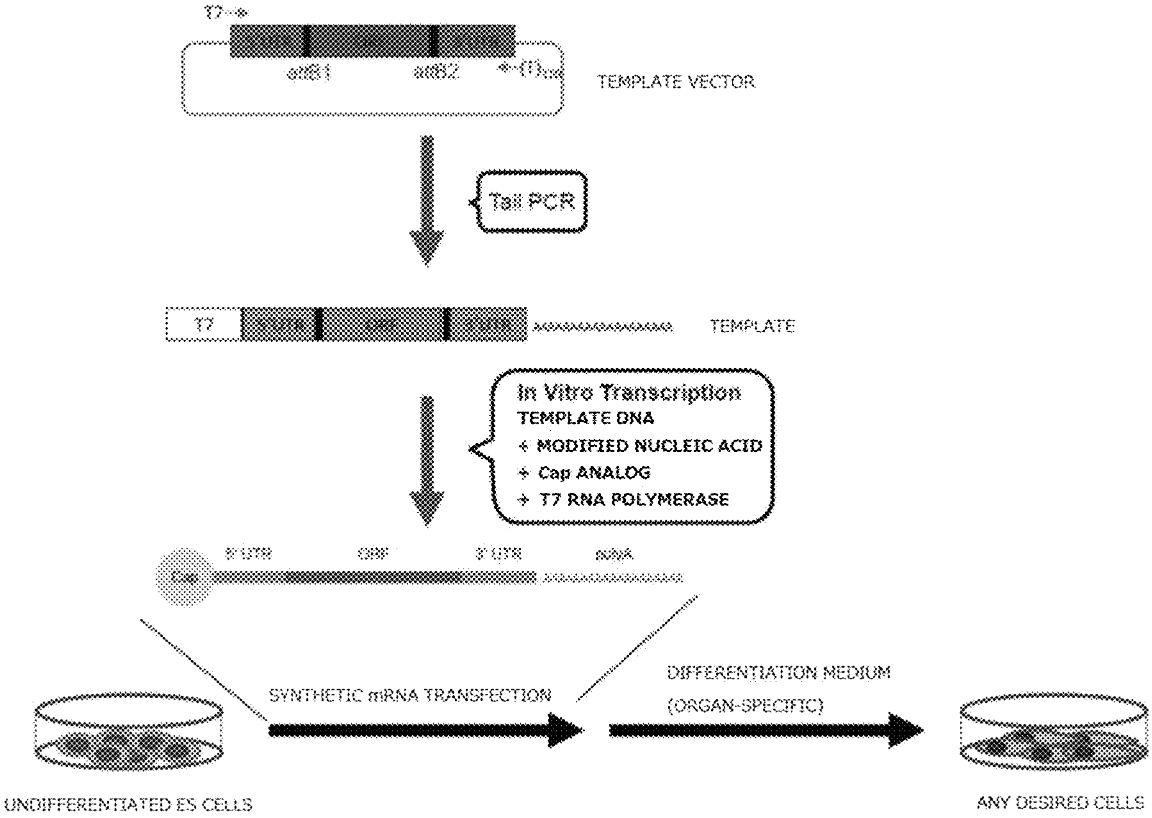
FIG. 3 A schematic view of a differentiation induction method using modified synthetic mRNA for a target gene.

In a step of the method of the present invention, a method known per se may be used without any particular limitation as a method of adding (introducing), to the pluripotent stem cell, the gene for the compound having an action of substantially removing or reducing an expression amount of a POU5F1 protein (or the gene for the compound having an action of substantially removing or reducing H3K27me3 modification) and/or the transcription factor required for induction of differentiation into the desired cell type. There is preferably used a method of inducing differentiation by efficiently introducing synthetic mRNA for a transcription factor into human pluripotent stem cells through use of a gene expression method involving using synthetic mRNA developed by Warren, Rossi, et al. (reference: Cell Stem Cell 7:618-630, 2010), which is a footprint-free forced gene expression method causing no gene incorporation into a host genome (see FIG. 3).

The timing at which the gene for the compound having an action of substantially removing or reducing an expression amount of a POU5F1 protein (or the gene for the compound having an action of substantially removing or reducing H3K27me3 modification) and the transcription factor required for induction of differentiation into the desired cell type are added to the pluripotent stem cell is not particularly limited, but it is preferred that the gene for the compound having an action of substantially removing or reducing an expression amount of a POU5F1 protein (or the gene for the compound having an action of substantially removing or reducing H3K27me3 modification) be added to the pluripotent stem cell before the addition of the transcription factor required for differentiation induction.

Further, with regard to the addition timing of each gene (mRNA), the addition may be performed, for example, one or more times, preferably two to five times, two to four times, two or three times, or two times every 12 hours to 64 hours, but the addition timing is not particularly limited thereto. A more specific method may be exemplified by the following.

(Synthesis of Modified mRNA Encoding Amino Acid Sequence of Transcription Factor)

Modified mRNA is synthesized with a referred method described in the literature "Warren et al., Cell Stem Cell, 2010 Nov. 5; 7 (5): 618-30." More specifically, mRNA is synthesized by in vitro transcription using a mixture of dNTPs {(dNTPs: 3-0-Me-$m^7$G(5')ppp(5')G ARCA cap analog, 5-methylcytidine triphosphate, and pseudouridine triphosphate)} obtained by modifying template DNA encoding the amino acid sequence of the transcription factor required for induction of differentiation into the desired cell type.

(Generation of Sendai Virus Vector Encoding Amino Acid Sequence of Transcription Factor)

In order to express a mammalian (in particular, human) transcription factor, a Sendai virus vector capable of expressing a human transcription factor is preferably used. In particular, a mutant of a Sendai virus vector, such as an F protein-deficient mutant, has no infectivity, and is easy to handle (see Inoue et al., J Virol. 77:23238-3246, 2003).

(Method of Inducing Differentiation of Pluripotent Stem Cell into Desired Cell Type with High Efficiency)

A single transcription factor or a cocktail of two or more transcription factors required for induction of differentiation into the desired cell type is prepared. The form of the transcription factors is not particularly limited, and may be any of synthetic mRNAs, a Sendai virus vector having incorporated therein a transcription factor (or a plurality of transcription factors), and nanoparticle capsules containing synthetic mRNAs.

Figure 4:
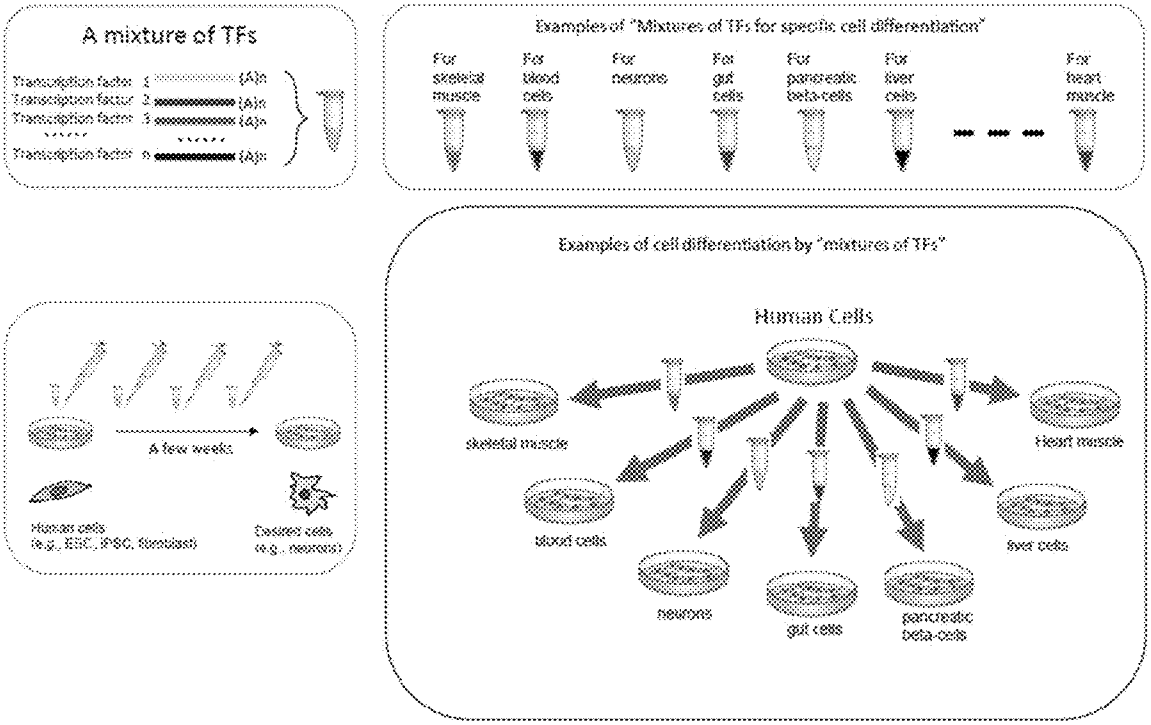
FIG. 4 A schematic view of a differentiation step using modified synthetic mRNA for a target gene.

A method of introducing the single transcription factor or cocktail of two or more transcription factors described above into cells is not particularly limited, and transfection with Lipofectamine, viral infection, or the like is utilized. A schematic view of one example of the differentiation induction step that may be utilized in the method of the present invention is illustrated in FIG. 4.

(Use of Expression Vector)

In a step of the method of the present invention, an expression vector known per se having introduced therein the gene for the compound having an action of substantially removing or reducing an expression amount of a POU5F1 protein (or the gene for the compound having an action of substantially removing or reducing H3K27me3 modification) and/or the transcription factor required for induction of differentiation into the desired cell type may be used. Examples of the expression vector to be used in the present invention may include, but not particularly limited to, an animal cell expression plasmid vector, a Sendai virus vector and others.

A method of introducing the synthetic mRNA and the expression vector into the pluripotent stem cell is not particularly limited, but examples thereof may include a lipofection method, a liposome method, an electroporation method, a calcium phosphate coprecipitation method, a diethylaminoethyl (DEAE)-dextran method, a microinjection method, a gene gun method and others. A particularly preferred example is a lipofection method.

Another method may involve using an expression vector for the gene for the compound having an action of substantially removing or reducing an expression amount of a POU5F1 protein (or the gene for the compound having an action of substantially removing or reducing H3K27me3 modification), and using synthetic mRNA for the transcription factor required for induction of differentiation into the desired cell type, or may adopt the opposite pattern.

(Compound Having Action of Substantially Removing or Reducing Expression Amount of POU5F1 Protein)

The compound having an action of substantially removing or reducing an expression amount of a POU5F1 protein of the present invention is not particularly limited, but is, for example, siRNA against POU5F1, shRNA against POU5F1, an antisense strand of POU5F1, an antibody that specifically binds to the POU5F1 protein, or an inhibitor.

In addition, not only by using those compounds alone, but also by using a plurality of kinds of compounds and/or a low-molecular-weight compound in combination, it is possible to efficiently "reduce an undifferentiated state of a pluripotent stem cell (substantially remove or reduce an expression amount of a POU5F1 protein in a pluripotent stem cell)."

(Compound Having Action of Substantially Removing or Reducing H3K27Me3 Modification)

The compound having an action of substantially removing or reducing H3K27me3 modification of the present invention is not particularly limited, but is, for example, a demethylase (in particular, a demethylase having an action of removing a methyl group of H3K27me3), an antibody that specifically binds to H3K27me3, an antibody for Polycomb-group proteins (PcG proteins) having an H3K27me3 modification action, siRNA (in particular, cationic siRNA), or an inhibitor. The cationic siRNA does not require a reagent for transfection.

Examples of the low-molecular-weight compound may include, but not particularly limited to, histone deaceylase (HDAC) inhibitors, such as valproic acid.

Examples of the demethylase include AOF (LSD1), AOF1 (LSD2), FBXL11 (JHDM1A), Fbx110 (JHDM1B), FBXL19 (JHDM1C), KIAA1718 (JHDM1D), PHF2 (JHDM1E), PHF8 (JHDM1F), JMJD1A (JHDM2A), JMJD1B (JHDM2B), JMJD1C (JHDM2C), JMJD2A (JHDM3A), JMJD2B (JHDM3B), JMJD2C (JHDM3C), JMJD2D (JHDM3D), RBP2 (JARID1A), PLU1 (JARID1B), SMCX (JARID1C), SMCY (JARID1D), Jumonji (JARID2), UTX (UTX), UTY (UTY), JMJD3 (JMJD3), JMJD4 (JMJD4), JMJD5 (JMJD5), JMJD6 (JMJD6), JMJD7 (JMJD7), and JMJD8 (JMJD8). Of those, JMJD3, UTX, or the like is preferred as a demethylase having an action of removing a methyl group of H3K27me3.

In addition, the demethylase of the present invention also includes the following:

(1) a protected derivative, sugar chain-modified derivative, acylated derivative, or acetylated derivative of any one of the demethylases described above;

(2) an enzyme that has 90% (or 92%, 94%, 96%, 98%, or 99%) or more homology to any one of the demethylases described above and has a substantially equivalent action of substantially removing or reducing H3K27me3 modification to that of the demethylase; and (3) an enzyme that has 100 to 10, 50 to 30, 40 to 20, 10 to 5, or 5 to 1 amino acid substituted, deleted, inserted, and/or added in any one of the demethylases described above and has a substantially equivalent action of substantially removing or reducing H3K27me3 modification to that of the demethylase.

Further, the gene of the demethylase of the present invention includes the following:

(1) a gene encoding a polypeptide formed of the amino acid sequence of any one or more of the enzymes described above;

(2) a gene encoding a polypeptide that has 1 to 20 (or 1 to 15, 1 to 10, 1 to 7, 1 to 5, or 1 to 3) amino acids substituted, deleted, inserted, and/or added in the amino acid sequence of any one or more of the enzymes described above and has a substantially equivalent action of substantially removing or reducing H3K27me3 modification to that of the demethylase; and (3) a gene encoding a polypeptide that has 90% (or 92%, 94%, 96%, 98%, or 99%) or more homology to the amino acid sequence of any one or more of the enzymes described above and has a substantially equivalent action of substantially removing or reducing H3K27me3 modification to that of the demethylase.

An enzyme having a mutation may be a naturally occurring one, or may be one obtained by introducing a mutation on the basis of a gene of natural origin. Means for introducing a mutation is known per se, and for example, a site-directed mutagenesis method, a homologous gene recombination method, a primer extension method, a polymerase chain reaction (hereinafter abbreviated as PCR), and the like may be used alone or in combination thereof as appropriate.

The method may be performed in conformity with any of methods described in the literatures ("Molecular Cloning: A Laboratory Manual, second edition" edited by Sambrook et al., 1989, Cold Spring Harbor Laboratory; and "Lab Manual: Genetic Engineering" edited by Masami Muramatsu, 1988, Maruzen), or by modifying these methods, and Ulmer's technology (Ulmer, K. M., "Science", 1983, volume 219, p. 666-671) may also be utilized. In the case of a peptide, from the viewpoint of preventing alteration of basic properties of the peptide (e.g., physical properties, function, physiological activity, or immunological activity) in the introduction of a mutation, for example, mutual substitution between homologous amino acids (e.g., polar amino acids, non-polar amino acids, hydrophobic amino acids, hydrophilic amino acids, positively charged amino acids, negatively charged amino acids, and aromatic amino acids) is easily conceivable.

(JMJD3)

JMJD3 is known as a demethylase for H3K27me3 of a histone (mouse NP_001017426, human NP_001073893), and even in its full length (NP_001073893, SEQ ID NO: 3), has an action of substantially removing or reducing the H3K27me3 modification of pluripotent stem cells. Surprisingly, the inventors of the present invention have confirmed that JMJD3c having the JmjC domain {SEQ ID NO: 4, catalytic domain: SEQ ID NO: 5 (amino acids 1376-1484)} has a stronger action of substantially removing or reducing H3K27me3 modification as compared to full-length JMJD3.

A preferred base sequence of JMJD3 is a base sequence set forth in SEQ ID NO: 32.

In addition, the JMJD3 of the present invention includes the following embodiments as well:

(1) a protected derivative, sugar chain-modified derivative, acylated derivative, or acetylated derivative of an amino acid sequence set forth in SEQ ID NO: 3;

(2) an amino acid sequence that has 90% (or 92%, 94%, 96%, 98%, or 99%) or more homology to the amino acid sequence set forth in SEQ ID NO: 3 and has a substantially equivalent action of substantially removing or reducing H3K27me3 modification to that of the JMJD3;

(3) an amino acid sequence that has 100 to 10, 50 to 30, 40 to 20, 10 to 5, or 5 to 1 amino acid substituted, deleted, inserted, and/or added in the amino acid sequence set forth in SEQ ID NO: 3 and has a substantially equivalent action of substantially removing or reducing H3K27me3 modification to that of the JMJD3;

(4) a protected derivative, sugar chain-modified derivative, acylated derivative, or acetylated derivative of an amino acid sequence set forth in SEQ ID NO: 4;

(5) an amino acid sequence that has 90% (or 92%, 94%, 96%, 98%, or 99%) or more homology to the amino acid sequence set forth in SEQ ID NO: 4 and has a substantially equivalent action of substantially removing or reducing H3K27me3 modification to that of the JMJD3c;

(6) an amino acid sequence that has 100 to 10, 50 to 30, 40 to 20, 10 to 5, or 5 to 1 amino acid substituted, deleted, inserted, and/or added in the amino acid sequence set forth in SEQ ID NO: 4 and has a substantially equivalent action of substantially removing or reducing H3K27me3 modification to that of the JMJD3c; and (7) an amino acid sequence that includes the amino acid sequence set forth in SEQ ID NO: 5 and has a substantially equivalent action of substantially removing or reducing H3K27me3 modification to the JMJD3c.

It is appropriate that the "sequence homology" be generally 70% or more, preferably 80%, more preferably 85% or more, still more preferably 90% or more, even more preferably 95% or more, most preferably 98% or more of an entire amino acid sequence.

In addition, the JMJD3 gene of the present invention includes the following:

(1) a gene encoding a polypeptide consisted of an amino acid sequence set forth in any one of SEQ ID NOS: 3 to 5;

(2) a gene encoding a polypeptide that has 1 to 20 (or 1 to 15, 1 to 10, 1 to 7, 1 to 5, or 1 to 3) amino acids substituted, deleted, inserted, and/or added in the amino acid sequence set forth in any one of SEQ ID NOS: 3 to 5 and has a substantially equivalent action of substantially removing or reducing H3K27me3 modification to that of the amino acid sequence set forth in any one of SEQ ID NOS: 3 to 5;

(3) a gene encoding a polypeptide that has 90% (or 92%, 94%, 96%, 98%, or 99%) or more homology to the amino acid sequence set forth in any one of SEQ ID NOS: 3 to 5 and has a substantially equivalent action of substantially removing or reducing H3K27me3 modification to that of the amino acid sequence set forth in any one of SEQ ID NOS: 3 to 5;

(4) a gene consisted of a base sequence set forth in any one of SEQ ID NOS: 6 to 8 and 32;

(5) a gene encoding a polypeptide that hybridizes with a base sequence complementary to the base sequence set forth in any one of SEQ ID NOS: 6 to 8 and 32 under stringent conditions and has a substantially equivalent action of substantially removing or reducing H3K27me3 modification to that of the amino acid sequence set forth in any one of SEQ ID NOS: 3 to 5;

(6) a gene that has a sequence of 1 to 50 (or 1 to 40, 1 to 30, 1 to 20, 1 to 15, 1 to 10, 1 to 5, or 1 to 3 bases substituted, deleted, inserted, and/or added in the DNA consisted of the base sequence set forth in any one of SEQ ID NOS: 6 to 8 and 32; and (7) a gene having 90% (or 92%, 94%, 96%, 98%, or 99%) or more homology to the gene formed of the base sequence set forth in any one of SEQ ID NOS: 6 to 8 and 32.

(Transcription Factor Required for Highly Efficient Induction of Differentiation into Desired Cell Type)

The embodiment of the "transcription factor required for highly efficient induction of differentiation into the desired cell type" to be used in the method of the present invention is not particularly limited, but examples thereof may include, but not particularly limited to, nucleic acids, such as RNA and DNA, synthetic nucleic acids, and proteins.

In addition, in the method of the present invention, examples of the desired cell type may include a skeletal muscle, the liver (hepatocytes), neurons, chondrocytes, bone cells, and hematopoietic cells.

{Transcription Factor Required for Induction of Differentiation into Skeletal Muscle (in Particular, Cells Present in Skeletal Muscle)}

A method of inducing differentiation into a skeletal muscle is as described below.

A single transcription factor, or two or more transcription factors selected from the group of MYOD1, NRF1, SALL4, ZIC1, KLF9, ZNF281, CTCF, HES1, HOXA2, TBX5, TP73, ERG, MAB21L3, PRDM1, NFIC, CTCFL, FOXP1, HEY1, PITX2, JUNB, KLF4, ESX1, TFAP2C, FOS, TFE3, FOSL1, GRHL2, TBX2, NFIB, and IRF4 are introduced into pluripotent stem cells. In particular, MYOD1 is preferably introduced into pluripotent stem cells.

{Transcription Factor Required for Induction of Differentiation into Liver (in Particular, Cells Present in Liver, i.e., Hepatoblasts)}

A method of inducing differentiation into the liver (in particular, the liver or the fetal liver) is as described below.

Liver: A single transcription factor, or two or more transcription factors selected from HNF1A, TCF-1, SALL4, TGIF1, MAB21L3, ZIC1, EGFLAM, PITX2, HNF4A, NRF1, ZNF281, CTCFL, TP73, TFE3, DLX6, and TCF4 are introduced into human pluripotent stem cells.

Fetal liver: A single transcription factor, or two or more transcription factors selected from HNF1A, TCF-1, SIX5, HNF4A, SIN3A, ID1, and HNF1A are introduced into human pluripotent stem cells.

In particular, HNF1A is preferably introduced into pluripotent stem cells.

(Transcription Factor Required for Induction of Differentiation into Neurons)

A method of inducing differentiation into neurons is as described below.

A single transcription factor, or two or more, three or more, four or more, or five transcription factors selected from NEUROG1, NEUROG2, NEUROG3, NEUROD1, and NEUROD2 are introduced into human pluripotent stem cells.

(Method of Introducing Target Gene into Genome of Pluripotent Stem Cell)

Figure 5:
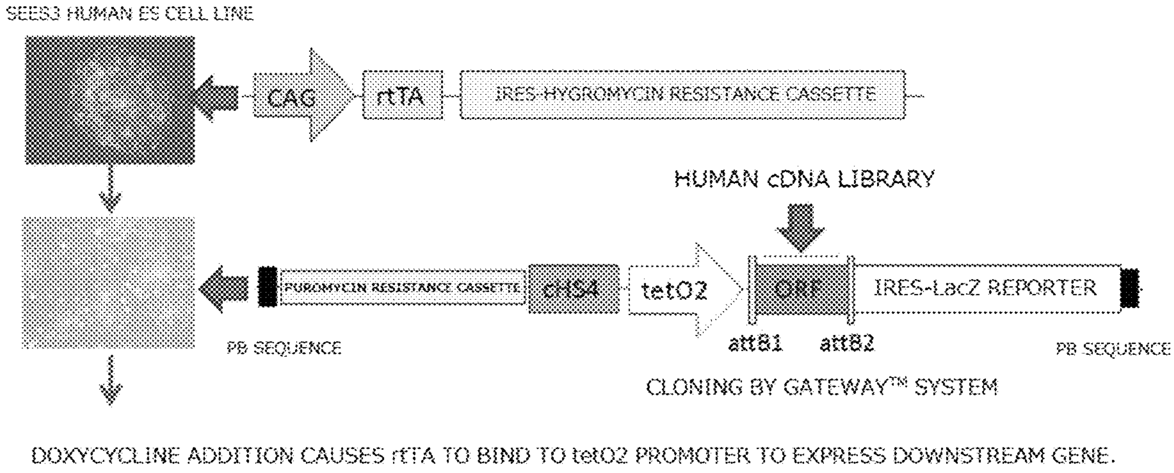
FIG. 5 A method of introducing a target gene into the genome of a pluripotent stem cell.

In a step of the method of the present invention, a method known per se may be used without any particular limitation as a method of introducing the gene for the compound having an action of substantially removing or reducing an expression amount of a POU5F1 protein (or the gene for the compound having an action of substantially removing or reducing H3K27me3 modification) and/or the transcription factor required for highly efficient induction of differentiation into the desired cell type into the genome of the pluripotent stem cell. There may be preferably used an expression cassette inserted between PiggyBac transposase recognition sequences (PB sequences) developed by Woltjen et al. (reference: Nature 458:766-770, 2009), which is a mechanism by which a gene to be introduced is actively incorporated into pluripotent stem cells (in particular, the genome of human ES cells). The expression cassette is a system capable of efficiently establishing a genetically modified pluripotent stem cell line by introducing a drug selection cassette (see FIG. 5).

(Method of Introducing Target Protein into Pluripotent Stem Cell)

In a step of the method of the present invention, a method known per se may be used as a method of introducing the compound having an action of substantially removing or reducing an expression amount of a POU5F1 protein (or the compound having an action of substantially removing or reducing H3K27me3 modification) (in particular, protein) and/or the transcription factor (protein) required for highly efficient induction of differentiation into the desired cell type into the genome of the pluripotent stem cell, and examples thereof may include: a method involving using a protein transfection reagent; a method involving using a fusion protein having added thereto a cell-penetrating peptide; and a microinjection method.

The "cell-penetrating peptide" of the present invention is a peptide having a property of migrating into a cell, more specifically a property of penetrating a cell membrane, still more specifically a property of penetrating a cell membrane or a nuclear membrane to penetrate into cytoplasm or a nucleus. The amino acid sequence of the peptide is not particularly limited, but examples thereof may include TAT (GRKKRRQRRRPQ: SEQ ID NO: 9), r8 {rrrrrrrr (D-form-R): SEQ ID NO: 10}, and MPG-8 (BAFLGWL-GAWGTMGWSPKKKRK: SEQ ID NO: 11).

The target protein encompasses both of the compound having an action of substantially removing or reducing an expression amount of a POU5F1 protein (or the compound having an action of substantially removing or reducing H3K27me3 modification) (in particular, protein) and/or the transcription factor (protein) required for highly efficient induction of differentiation into the desired cell type.

(Gene Knockout Method)

A gene knockout method is available as a method other than the foregoing. A "pluripotent stem cell in which a POU5F1 gene has been disrupted" may be generated by the gene knockout method. The "pluripotent stem cell in which a POU5F1 gene has been disrupted" means that normal expression of the POU5F1 gene is inhibited due to artificial modification of the sequence of a POU5F1 gene region, and as a result, the expression of POU5F1 is suppressed and a POU5F1 protein is not normally expressed.

In addition, the "whole" in "modification or deletion of part or the whole of the POU5F1 gene" refers to the protein-coding region of POU5F1 genomic DNA.

In addition, the "part" refers to a region that is part of the protein-coding region and that has a length required for inhibiting normal expression of the POU5F1 gene.

Further, the "modification" refers to modification of the base sequence of a target region in genomic DNA into another base sequence by substituting, deleting, inserting, and/or adding a single nucleotide or two or more of nucleotides.

(Differentiation Induction Kit for Inducing Differentiation of Pluripotent Stem Cell into Desired Cell Type with High Efficiency)

A differentiation induction kit for inducing differentiation of a pluripotent stem cell into a desired cell type with high efficiency of the present invention (hereinafter sometimes referred to as "kit of the present invention") includes any one or more of the following modes.

(1) Pluripotent Stem Cell in which Expression Amount of POU5F1 Protein has been Substantially Removed or Reduced and/or H3K27Me3 Modification has been Substantially Removed or Reduced A pluripotent stem cell in which an expression amount of a POU5F1 protein has been substantially removed or reduced and/or H3K27me3 modification has been substantially removed or reduced can be easily generated by the method of the present invention described above.

A implementer can easily induce differentiation into the desired cell type by introducing the transcription factor required for induction of differentiation into the desired cell type as described above into the pluripotent stem cell.

In addition, such pluripotent stem cell encompasses a pluripotent stem cell having a gene construct inducible with doxycycline or the like inserted into the genome thereof so that a gene for a compound having an action of substantially removing or reducing an expression amount of a POU5F1 protein, a demethylase, or the like can be transiently forcibly expressed therein.

(2) Gene for Compound Having Action of Substantially Removing or Reducing Expression Amount of POU5F1 Protein and/or Demethylase Gene for Kit of the Present Invention The implementer can easily generate the pluripotent stem cell in which an expression amount of a POU5F1 protein has been substantially removed or reduced and/or H3K27me3 modification has been substantially removed or reduced by adding a gene for a compound having an action of substantially removing or reducing an expression amount of a POU5F1 protein and/or a demethylase gene for a kit to a pluripotent stem cell.

Examples of the anti-POU5F1 antibody gene for a kit may include, but not particularly limited to, commercially available antibody genes.

Examples of the demethylase gene for a kit may include, but not particularly limited to, mRNAs, DNAs, and proteins of demethylase genes (e.g., JMJD3c).

(3) Gene for Compound Having Action of Substantially Removing or Reducing Expression Amount of POU5F1 Protein and/or Demethylase Gene, and Gene Containing Transcription Factor Required for Induction of Differentiation into Desired Cell Type for Kit of the Present Invention The implementer can easily generate the pluripotent stem cell in which an expression amount of a POU5F1 protein has been substantially removed or reduced and/or H3K27me3 modification has been substantially removed or reduced, and further, can induce differentiation thereof into the desired cell type with high efficiency by adding a gene for a compound having an action of substantially removing or reducing an expression amount of a POU5F1 protein and/or a demethylase gene, and a gene containing a transcription factor required for induction of differentiation into the desired cell type for a kit to a pluripotent stem cell.

Those genes may be present on one gene, or on separate genes. When the genes are present on separate genes, the gene for the compound having an action of substantially removing or reducing an expression amount of a POU5F1 protein (or demethylase gene) and the transcription factor required for induction of differentiation into the desired cell type may be added to the pluripotent stem cell simultaneously or at separate times.

(4) Compound Having Action of Substantially Removing or Reducing Expression Amount of POU5F1 Protein and/or Demethylase for Kit of the Present Invention The implementer can easily generate the pluripotent stem cell in which an expression amount of a POU5F1 protein has been substantially removed or reduced and/or H3K27me3 modification has been substantially removed or reduced by adding a compound having an action of substantially removing or reducing an expression amount of a POU5F1 protein and/or a demethylase for a kit to a pluripotent stem cell.

(5) Gene Construct Carrying Gene for Compound Having Action of Substantially Removing or Reducing Expression Amount of POU5F1 Protein and/or Demethylase Gene The user can easily generate the pluripotent stem cell in which an expression amount of a POU5F1 protein has been substantially removed or reduced and/or H3K27me3 modification has been substantially removed or reduced by introducing a gene construct carrying a gene for a compound having an action of substantially removing or reducing an expression amount of a POU5F1 protein and/or a demethylase gene into the genome of a pluripotent stem cell.

The gene construct may contain a promoter sequence, a gene expression-enhancing sequence, a marker gene, a reporter sequence, a drug resistance gene, and the like as required in addition to the gene for the compound having an action of substantially removing or reducing an expression amount of a POU5F1 protein and/or the demethylase gene.

(6) Gene Construct Carrying: Gene for Compound Having Action of Substantially Removing or Reducing Expression Amount of POU5F1 Protein and/or Demethylase Gene; and Transcription Factor Required for Induction of Differentiation into Desired Cell Type The implementer can easily generate the pluripotent stem cell in which an expression amount of a POU5F1 protein has been substantially removed or reduced and/or H3K27me3 modification has been substantially removed or reduced, and further, can induce differentiation thereof into the desired cell type by introducing a gene construct carrying: a gene for a compound having an action of substantially removing or reducing an expression amount of a POU5F1 protein and/or a demethylase gene; and a transcription factor required for induction of differentiation into the desired cell type into the genome of a pluripotent stem cell.

Those genes may be present on one gene, or on separate genes. When the genes are present on separate genes, the gene for the compound having an action of substantially removing or reducing an expression amount of a POU5F1 protein and/or the demethylase gene, and the transcription factor required for induction of differentiation into the desired cell type may be expressed in the genome of the pluripotent stem cell simultaneously or at separate times.

The gene construct may contain a promoter sequence, a gene expression-enhancing sequence, a marker gene, a reporter sequence, a drug resistance gene, and the like as required in addition to the gene for the compound having an action of substantially removing or reducing an expression amount of a POU5F1 protein and/or the demethylase gene, and the transcription factor required for induction of differentiation into the desired cell type.

(Proteins Associated with Undifferentiated State Maintenance Other than POU5F1)

NANOG, SOX2, SOX3, KLF2, KLF4, KLF5, TBX3, ESRRB, SALLA, STAT3, ZIC3, LIN28, and TCF3 are known as proteins associated with undifferentiated state maintenance. Accordingly, it is considered that pluripotent stem cells in which expression amounts of the proteins of NANOG, SOX2, SOX3, KLF2, KLF4, KLF5, TBX3, ESRRB, SALL4, STAT3, ZIC3, LIN28, and TCF3 have been substantially removed or reduced can be differentiated into the desired cell type with high efficiency.

Further, a pluripotent stem cell in which an expression amount of any one or more of the above-mentioned proteins has been substantially removed or reduced and an expression amount of a POU5F1 protein has been substantially removed or reduced (pluripotent stem cell in which an expression amount of any one or more of the above-mentioned proteins has been substantially removed or reduced and an expression amount of a POU5F1 protein has been substantially removed or reduced, and which has a histone in which H3K27me3 modification has been substantially removed or reduced) is also included in the present invention.

In addition, a method of differentiating a pluripotent stem cell into a desired cell type including a step of adding a gene for a compound having an action of substantially removing or reducing an expression amount of any one or more of the above-mentioned proteins, a gene for a compound having an action of substantially removing or reducing an expression amount of a POU5F1 protein (further, a demethylase gene or the like), and a transcription factor required for induction of differentiation into the desired cell type to a pluripotent stem cell is also encompassed in the present invention.

A method of differentiating a pluripotent stem cell into a desired cell type of the present disclosure may be exemplified by, but not particularly limited to, a method including any one of the following steps (1) to (9):

(1) a step of adding a gene for a compound having an action of substantially removing or reducing an expression amount of a POU5F1 protein and a transcription factor required for induction of differentiation into the desired cell type to a pluripotent stem cell;
(2) a step of inserting a gene construct carrying a gene for a compound having an action of substantially removing or reducing an expression amount of a POU5F1 protein and a transcription factor gene required for induction of differentiation into the desired cell type, into a genome of a pluripotent stem cell;
(3) a step of inserting a gene construct carrying a gene for a compound having an action of substantially removing or reducing an expression amount of a POU5F1 protein and a gene construct carrying a transcription factor required for induction of differentiation into the desired cell type, into a genome of a pluripotent stem cell;
(4) a step of adding a transcription factor required for induction of differentiation into the desired cell type to a pluripotent stem cell in which an expression amount of a POU5F1 protein has been substantially removed or reduced;
(5) a step of adding a transcription factor required for induction of differentiation into the desired cell type to a pluripotent stem cell in which a compound having an action of substantially removing or reducing an expression amount of a POU5F1 protein is forcibly expressed;
(6) a step of adding a compound having an action of substantially removing or reducing an expression amount of a POU5F1 protein and a transcription factor required for differentiation into the desired cell type to a pluripotent stem cell;
(7) a step of adding a transcription factor required for induction of differentiation into the desired cell type to a pluripotent stem cell in which a POU5F1 gene has been disrupted;
(8) a step of adding a gene for a compound having an action of substantially removing or reducing an expression amount of a POU5F1 protein, a demethylase gene, and a transcription factor required for induction of differentiation into the desired cell type to a pluripotent stem cell; and
(9) a step of adding a transcription factor required for induction of differentiation into the desired cell type to a pluripotent stem cell in which an expression amount of a POU5F1 protein has been substantially removed or reduced and which has a histone in which H3K27me3 modification has been substantially removed or reduced.

The present disclosure also includes any one of the following pluripotent stem cells for differentiation into a desired cell type:

(1) a pluripotent stem cell for differentiation into a desired cell type, in which an expression amount of a POU5F1 protein has been substantially removed or reduced;

(2) a pluripotent stem cell for differentiation into a desired cell type, in which a gene for a compound having an action of substantially removing or reducing an expression amount of a POU5F1 protein is forcibly expressed;

(3) a pluripotent stem cell for differentiation into a desired cell type, which has a gene construct carrying a gene for a compound having an action of substantially removing or reducing an expression amount of a POU5F1 protein inserted into the genome thereof;

(4) a pluripotent stem cell for differentiation into a desired cell type, in which a POU5F1 gene has been disrupted; and (5) a pluripotent stem cell for differentiation into a desired cell type, in which an expression amount of a POU5F1 protein has been substantially removed or reduced and which has a histone in which H3K27me3 modification has been substantially removed or reduced.

The present disclosure also includes a use of any one of the following pluripotent stem cells for differentiation into a desired cell type:

(1) a pluripotent stem cell for differentiation into a desired cell type, in which an expression amount of a POU5F1 protein has been substantially removed or reduced;

(2) a pluripotent stem cell for differentiation into a desired cell type, in which a gene for a compound having an action of substantially removing or reducing an expression amount of a POU5F1 protein is forcibly expressed;

(3) a pluripotent stem cell for differentiation into a desired cell type, which has a gene construct carrying a gene for a compound having an action of substantially removing or reducing an expression amount of a POU5F1 protein inserted into the genome thereof;

(4) a pluripotent stem cell for differentiation into a desired cell type, in which a POU5F1 gene has been disrupted; and (5) a pluripotent stem cell for differentiation into a desired cell type, in which an expression amount of a POU5F1 protein has been substantially removed or reduced and which has a histone in which H3K27me3 modification has been substantially removed or reduced.

The present disclosure also includes a use of any one of the following pluripotent stem cells for differentiation into a desired cell type, in production of a differentiation induction kit for differentiating a pluripotent stem cell into a desired cell type:

(1) a pluripotent stem cell for differentiation into a desired cell type, in which an expression amount of a POU5F1 protein has been substantially removed or reduced;

(2) a pluripotent stem cell for differentiation into a desired cell type, in which a gene for a compound having an action of substantially removing or reducing an expression amount of a POU5F1 protein is forcibly expressed;

(3) a pluripotent stem cell for differentiation into a desired cell type, which has a gene construct carrying a gene for a compound having an action of substantially removing or reducing an expression amount of a POU5F1 protein inserted into the genome thereof;

(4) a pluripotent stem cell for differentiation into a desired cell type, in which a POU5F1 gene has been disrupted; and (5) a pluripotent stem cell for differentiation into a desired cell type, in which an expression amount of a POU5F1 protein has been substantially removed or reduced and which has a histone in which H3K27me3 modification has been substantially removed or reduced.

The present invention is more embodied described below by Examples. However, the present invention is not limited to these Examples. All of these Examples have been approved by the Ethics Committee of Keio University School of Medicine.

Example 1

Materials and Methods

Examples 2 to 6 were carried out using materials and methods described below. The details are as described below.

(Human Pluripotent Stem Cell Culture and Differentiation Induction Methods)

Human ES cell (hESC) lines SEES-3 and H9 were obtained from the National Center for Child Health and Development (National Research Institute for Child Health and Development) and the Cell Research Institute, USA, respectively. A human induced pluripotent stem cell (hiPSC) line was obtained from RIKEN or the Center for iPS Cell Research and Application, Kyoto University. hESC/iPSCs were cultured using StemFit AK-03 medium (Ajinomoto) on iMatrix-511 (Nippi)-coated plates without use of feeder cells. A ROCK (Rho-associated coiled-coil forming kinase/Rho-associated kinase) inhibitor Y-27632 was added to the medium during cell subculture in order to inhibit apoptosis induced by cell detachment during cell passaging.

For myogenic differentiation, the hESC/iPSCs were cultured in a medium of αMEM (Gibco) supplemented with 5% KSR, 1 mM sodium pyruvate, 0.1 mM non-essential amino acids, 2 mM glutamine, 0.1 mM β-mercaptoethanol, and penicillin/streptomycin (50 U/50 μg/ml) on iMatrix-511-coated plates.

For albumin secretion hepatocyte differentiation, the hESC/iPSCs were cultured in the above-mentioned medium on Matrigel (BD)-coated plates, then cultured in RPMI 1640 medium supplemented with 1 mM NaB, 100 ng/ml Activin A, 50 ng/ml Wnt3a, 1×B27, and 2 mM GlutaMAX for 1 day, subsequently cultured in DMEM medium supplemented with 1% DMSO, 0.5 mM MTG, 1% NEAA, 1 mM GlutaMAX, and 20% KSR for 5 days, and finally cultured in HCM medium (Lonza) supplemented with 20 ng/ml HGF and 20 ng/ml Oncostatin M for 7 days.

(siRNA Transfection)

siRNA against POU5F1 (sense strand: GCCCGAAAGAGAAAGCGAATT: SEQ ID NO: 12, antisense strand: UUCGCUUUCUCUUUCGGGCCT: SEQ ID NO: 13) identical to that used in the literature "Proceeding of national academy of sciences 109, 4485-4490 (2012)" was purchased from Applied Biosystems and used (product number: s10873). siRNA serving as a negative control was also purchased from Applied Biosystems and used. siRNA transfections were performed with Lipofectamine Messenger Max (Invitrogen), according to the instructions of the accompanying manual. The B18R interferon inhibitor (eBioscience) was added to the culture medium to increase the viability of the transfected cells. The medium was replaced 2 hours to 3 hours after each transfection.

(Modified mRNA Synthesis and Transfection)

The protein-coding regions (Open Reading Frames, ORFs) of a red fluorescent protein mCherry, a green fluorescent protein Emerald, and tissue-specific transcription factors {MYOD1 (SEQ ID NO: 26), HNF1A (SEQ ID NO: 27), RUNX2 (SEQ ID NO: 28), SOX9 (SEQ ID NO: 29), SPI1 (SEQ ID NO: 30), and ASCL1 (SEQ ID NO: 31)} were subcloned into a pCRII construct containing the 5' UTR and 3' UTR of mouse α-globin, which increased mRNA stability and translation efficiency, to prepare templates used to synthesize mRNAs.

Modified mRNAs were synthesized on the basis of the description of the literature "Cell stem cell 7, 618-630 (2010)". Briefly speaking, a T7 promoter and a poly(A) tail were added through PCR reaction using a KAPA taq kit (Kapa Biosystems). RNAs were synthesized from PCR products using a MEGAscript T7 kit (Ambion) together with ARCA cap analog (New England Biolabs), ATP, GTP, 5-Methyl-CTP (TriLink), and pseudo-UTP (TriLink). The synthetic mRNAs were purified using a MEGAclear kit (Ambion). Synthetic mRNA transfections were performed with Lipofectamine MessengerMax (Invitrogen) according to the instructions of the accompanying manual. The B18R interferon inhibitor (eBioscience) was added to the culture medium to increase the viability of the transfected cells. The medium was replaced 2 hours to 3 hours after each transfection.

(Antibody)

The following antibodies were used:

POU5F1 (Santa Cruz, sc-5279);

β-ACTIN (Cell Signaling, 4970S);

MyHC (R&D MAB4470);

ALBUMIN (Abcam ab10241); and

AFP (R&D MAB1368).

(Immunostaining)

The cells were fixed in 4% PFA for 10 minutes at room temperature and permeabilized in 0.5% Triton-X-containing PBS for 10 minutes. The cells were treated a blocking in 2% BSA-containing PBS for 10 minutes, and cultured with primary antibodies in a blocking solution (1:500) for from 2 hours to 3 hours at room temperature or overnight at 4° C. The cells were washed twice in PBS, and then cultured with Alexa dye-conjugated secondary antibodies (Invitrogen) in a blocking solution (1:500) for 1 hour at room temperature. Nuclei were counterstained with DAPI (Dako). Immunofluorescence was visualized with an inverted fluorescence microscope IX73 (Olympus). Images were obtained using Olympus cellSens imaging software.

(Immunoblotting Method)

The cells were lysed with a sample buffer (50 mM Tris-HCl, pH 6.8, 2% SDS, 6% 2-mercaptoethanol, and 500 mg/ml urea). The proteins were separated by SDS-PAGE using a 4-15% polyacrylamide gel (Biorad) and were electrically transferred to polyvinylidene fluoride membranes (Biorad). The membranes were blocked for 1 hour in 0.1% Tween-20-containing Tris-buffered saline (TBST) and 5% skimmed milk. The membranes were washed in TBST and then incubated with primary antibodies in 2% BSA-containing TBS (1:1,000 dilution) for from 2 hours to 3 hours at room temperature or overnight at 4° C. The membranes were washed and incubated with horseradish peroxidase-conjugated secondary antibodies (GE) for 1 hour at room temperature. The membranes were washed in TBST, and immunoreactivity was visualized using ECL Prime Detection Kit (GE) and detected using Luminescent Image Analyzer (LAS-4000; Fujifilm).

(qRT-PCR)

Total RNA was isolated with TRIzol reagent (Invitrogen), and cDNAs were generated with random hexamers using a ReverTra Ace kit (Toyobo). Real-time PCR was performed using a SYBR Green PCR system (Takara). The primer sequences used for RT-PCR are listed below.

MYOG primer (Forward): gccagactatccccttcctc (SEQ ID NO: 14)

MYOG primer (Reverse): gaggccgcgttatgataaaa (SEQ ID NO: 15)

AFP primer (Forward): tgggacccgaactttcca (SEQ ID NO: 16)

AFP primer (Reverse): ggccacatccaggactagtttc (SEQ ID NO: 17)

COL1A1 primer (Forward): cctggatgccatcaaagtct (SEQ ID NO: 18)

COL1A1 primer (Reverse): tcttgtccttggggttcttg (SEQ ID NO: 19)

COL2A1 primer (Forward): tttcccaggtcaagatggtc (SEQ ID NO: 20)

COL2A1 primer (Reverse): cttcagcacctgtctcacca (SEQ ID NO: 21)

CD45 primer (Forward): tcctggactcccaaaatctg (SEQ ID NO: 22)

CD45 primer (Reverse): accttgaacccgaacatgag (SEQ ID NO: 23)

NESTIN primer (Forward): tggttttccagagtcttcagtga (SEQ ID NO: 24)

NESTIN primer (Reverse): gaaacagccatagagggcaaa (SEQ ID NO: 25)

Example 2

(Pluripotent Stem Cells in which Expression Amount of POU5F1 Protein has been Reduced)

In this Example, it was confirmed whether pluripotent stem cells in which the expression amount of a POU5F1 protein had been forcibly reduced were able to be generated or not. The details are as described below.

(Confirmation of Suppression of Expression of POU5F1 by siRNA Transfection)

Figure 6:
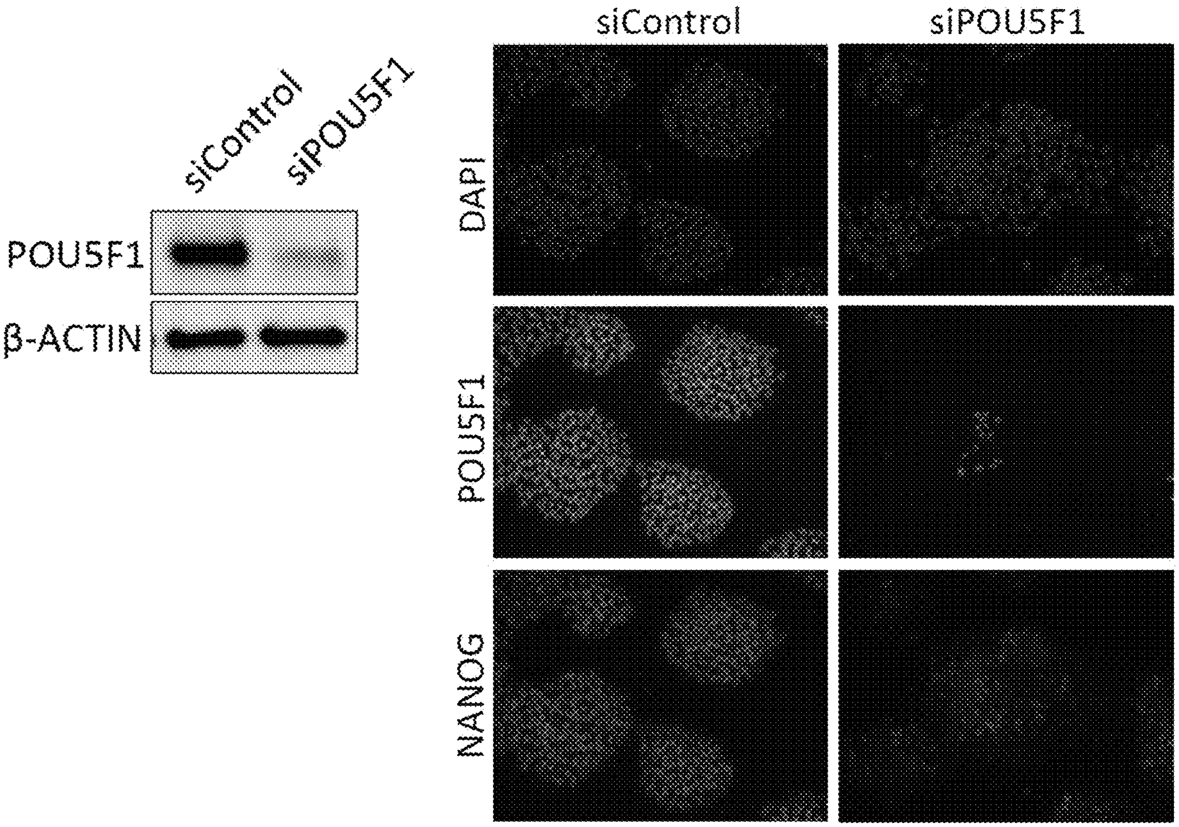
FIG. 6 The suppression of the expression of the POU5F1 protein by siRNA. Human ES cells were transfected with siRNA of POU5F1 (siPOU5F1), and it was confirmed by western blot using a specific antibody that the protein of POU5F1 was decreased (left figures) and it was confirmed by an immunostaining method using a specific antibody that the proteins of POU5F1 and NANOG were decreased (right figures). As a control, scramble siRNA (siControl) not acting on any gene was used. β-ACTIN represents a "loading control", and DAPI represents "cell nuclei".

Effects of siRNA (siPOU5F1) on POU5F1 in human ES cells were confirmed by an immunoblotting method and an immunostaining method (FIG. 6). Cells on Day 3 after siPOU5F1 transfection were analyzed, and as a result, it was confirmed that the POU5F1 protein was significantly decreased as compared to cells transfected with negative control siRNA (scramble siRNA sequence against POU5F1: siControl) (FIG. 6). The siPOU5F1 transfection decreased an NANOG protein serving as a molecular marker for pluripotent stem cells.

Thus, the disappearance of pluripotency by the siPOU5F1 transfection was confirmed.

(Confirmation of Morphological Change of Human ES Cells by siPOU5F1 Transfection)

Figure 7:
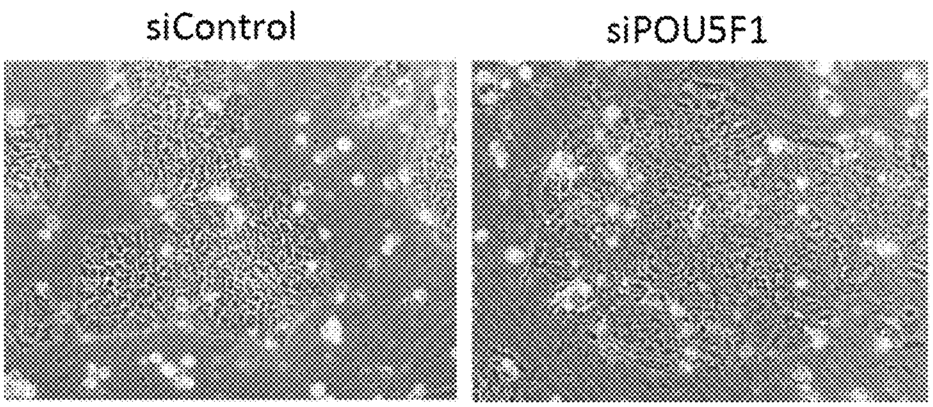
FIG. 7 The morphological change of pluripotent stem cells by siPOU5F1. It is shown that human ES cells changed into flat shapes when transfected with siPOU5F1.

Human ES cells have small round shapes when their undifferentiated state is maintained. It was confirmed that cells underwent a morphological change into flat shapes when transfected with siPOU5F1, and were directed toward differentiation through POU5F1 suppression (FIG. 7).

As this Example's result, it was confirmed that pluripotent stem cells in which the expression amount of the POU5F1 protein had been reduced were able to be generated, and that the cells were promoted toward differentiation.

Example 3

(Confirmation of Induction of Differentiation of Pluripotent Stem Cells in which Expression Amount of POU5F1 Protein has been Reduced into Desired Cell Types)

In this Example, it was confirmed whether differentiation into desired cell types was induced by introducing (adding) transcription factors required for induction of differentiation into the desired cell types to pluripotent stem cells in which the expression amount of the POU5F1 protein had been reduced. The details are as described below.

siPOU5F1 and modified synthetic RNAs (synRNAs) for a tissue-specific transcription factors were introduced into human ES cells, and the expression of differentiation marker genes MYOG (skeletal muscles), AFP (hepatocytes), COL1A1 (bone cells), COL2A1 (cartilage), CD45 (hematopoietic cells), and NESTIN (nerves) was examined by a real-time RT-PCR method.

Figure 8:
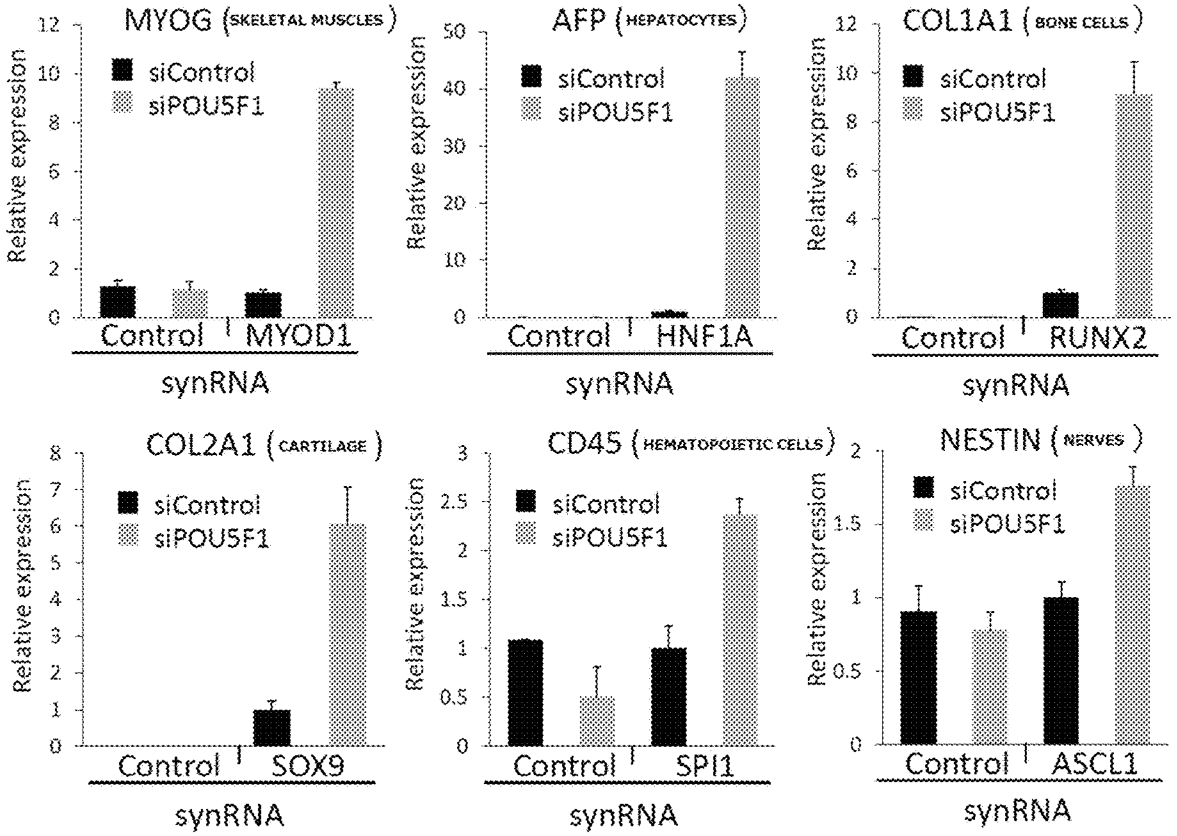
FIG. 8 It is shown that the co-transfection of siPOU5F1 and transcription factor mRNA activates differentiation genes. It was confirmed by a real-time PCR method that the transfection of human ES cells with modified synthetic RNAs (synRNAs) for tissue-specific transcription factors (MYOD1, HNF1A, RUNX2, SOX9, SPI1, and ASCL1) in combination with siPOU5F1 increased the expression of respective differentiation marker genes (MYOG, AFP, COL1A1, COL2A1, CD45, and NESTIN). Right bars represent cases of transfection with siPOU5F1, and left bars represent cases of transfection with siControl. mCherry or Emerald was used as synRNA serving as a negative control.

As the tissue-specific transcription factors, MYOD1 (skeletal muscles), HNF1A (liver), RUNX2 (bone cells), SOX9 (cartilage), SPI1 (blood), and ASCL1 (nerves) were used. As a negative control, synRNA for mCherry or Emerald was introduced.

siControl or siPOU5F1 and synRNA were simultaneously introduced (added) to the cells, and 1 day after that, the synRNA was further introduced thereto twice. The next day (2 days after the first introduction), the cells were sampled and analyzed. The medium used was a medium for undifferentiated state maintenance. As a result, it was confirmed that, when siPOU5F1 was introduced in combination with the transcription factors, the expression of the differentiation markers for the respective tissues was significantly increased (FIG. 8). While, as siControl or the transcription factors were introduced alone, any increases in expression of the differentiation markers were hardly detected (FIG. 8).

As this Example's result, it was confirmed that differentiation into desired cell types was efficiently induced by introducing (adding) the transcription factors required for induction of differentiation into the desired cell types to the pluripotent stem cells in which the expression amount of the POU5F1 protein had been reduced.

Example 4

(Confirmation of Differentiation of Pluripotent Stem Cells in which Expression Amount of POU5F1 Protein has been Reduced into Desired Cell Types)

In this Example, as examples of induction of differentiation into desired cell types, a myogenic differentiation (skeletal muscle cell differentiation) model using a myogenesis-regulating master transcription factor MYOD1, and a hepatocyte differentiation model using hepatocyte nuclear factor-1-alpha (HNF1A) were adopted. It is known that forced expression of MYOD1 alone cannot cause sufficient epigenetic changes and transcriptional changes in hESCs, resulting in poor myogenic conversion (see Cell reports 3, 661-670 (2013)).

(Skeletal Muscle Cell Differentiation)

Human ES cells were co-transfected with siControl or siPOU5F1 and synRNA for MYOD1 (MYOD1-synRNA), and 1 day after that, were further transfected twice with MYOD1-synRNA. In this case, the cells were cultured in a skeletal muscle differentiation medium.

Two days after the last synRNA transfection, which was performed 2 days after the first transfection, the cells were fixed and immunostained. The ES cells transfected with siControl hardly underwent a morphological change even when transfected with MYOD1-synRNA, and few of the cells expressed Myosin Heavy Chain (MyHC) serving as a terminal differentiation marker for a skeletal muscle (FIG. 9).

Figure 9:
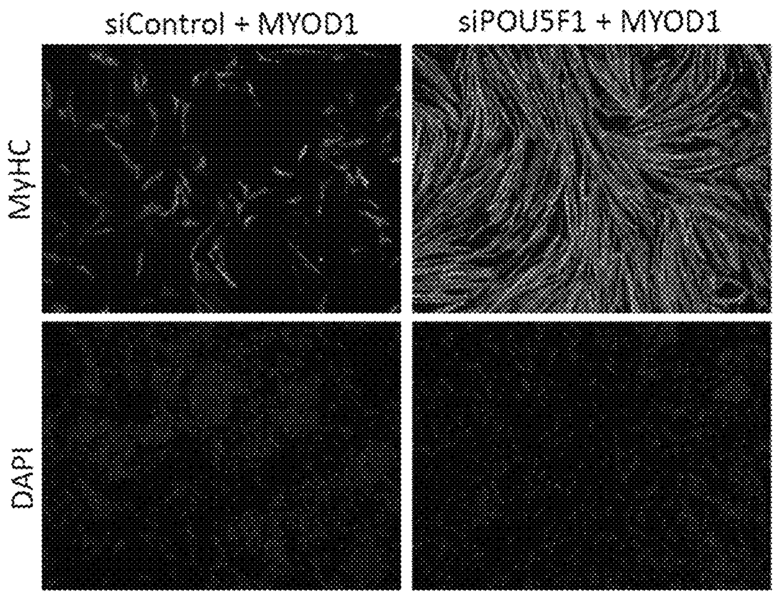
FIG. 9 Skeletal muscle differentiation by siPOU5F1 and MYOD1-synRNA was confirmed by an immunostaining method using an MyHC antibody. It was confirmed that, although MYOD1 alone (siControl+MYOD1) hardly caused muscle differentiation, its combination with siPOU5F1 dramatically induced muscle differentiation. MyHC represents a "terminal differentiation marker", and DAPI represents "cell nuclei".

However, as the ES cells transfected with siPOU5F1 were used, 2 days after the last MYOD1-synRNA transfection, fibrous muscle cells appeared at a high frequency and most of the cells were MyHC-positive, confirming that the cells were differentiated into skeletal muscle cells (FIG. 9).

Figure 10:
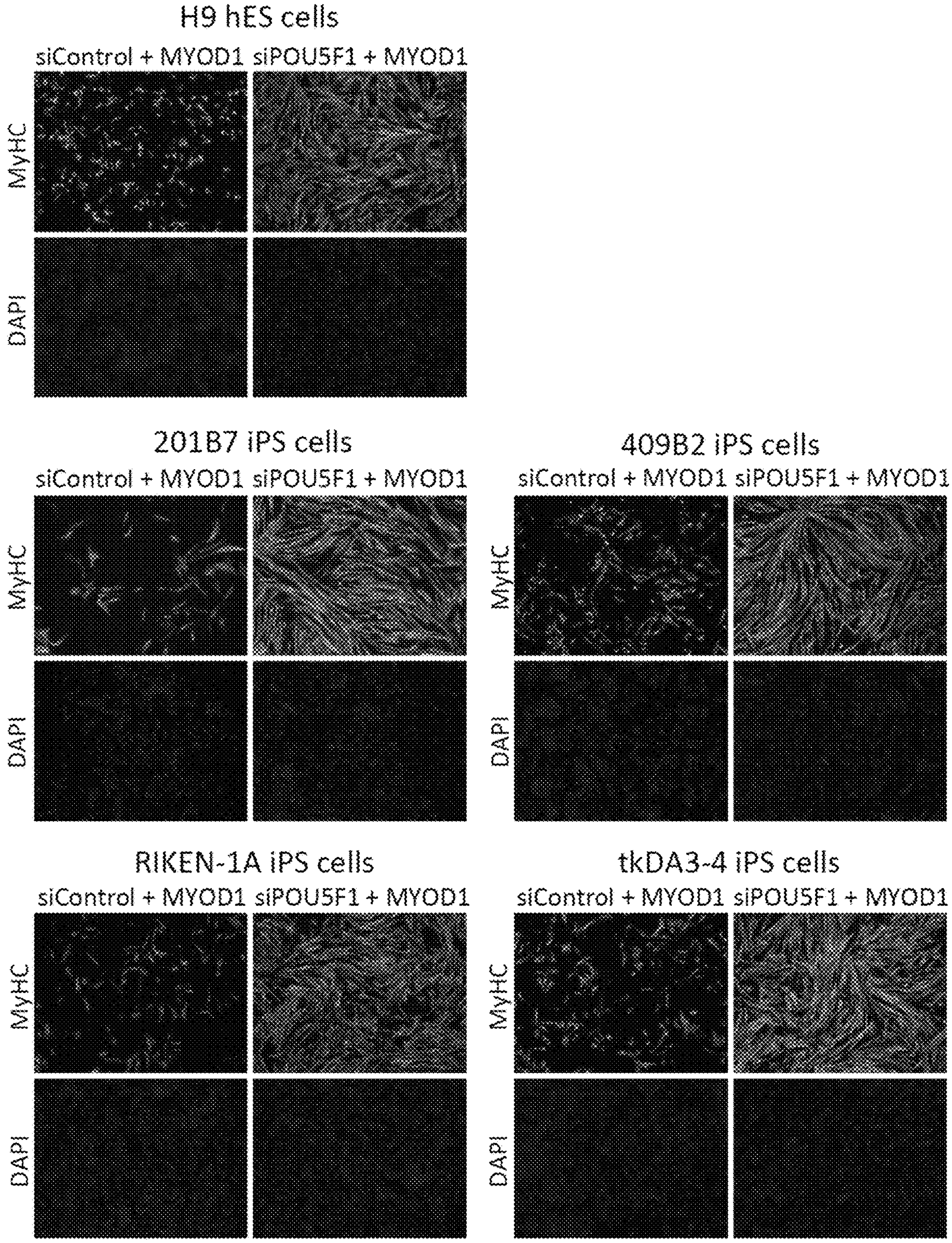
FIG. 10 Skeletal muscle differentiation in more than one ES cell lines and iPS cell lines by siPOU5F1 and MYOD1-synRNA was confirmed by an immunostaining method using an MyHC antibody. The co-expression of siPOU5F1 and MYOD1-synRNA was able to induce skeletal muscle differentiation rapidly and with high efficiency also in an H9 line serving as an ES cell line, and four kinds of iPS cell lines (201B7, 409B2, RIKEN-1A, and tkDA3-4).

In addition, similar effects were also able to be obtained in another ES cell line (H9 hES cell) and a plurality of iPS cell lines (201B7 iPS cell, 409B2 iPS cell, RIKEN-1A iPS cell, and tkDA3-4 iPS cell) (FIG. 10).

(Hepatocyte Differentiation)

Figure 11:
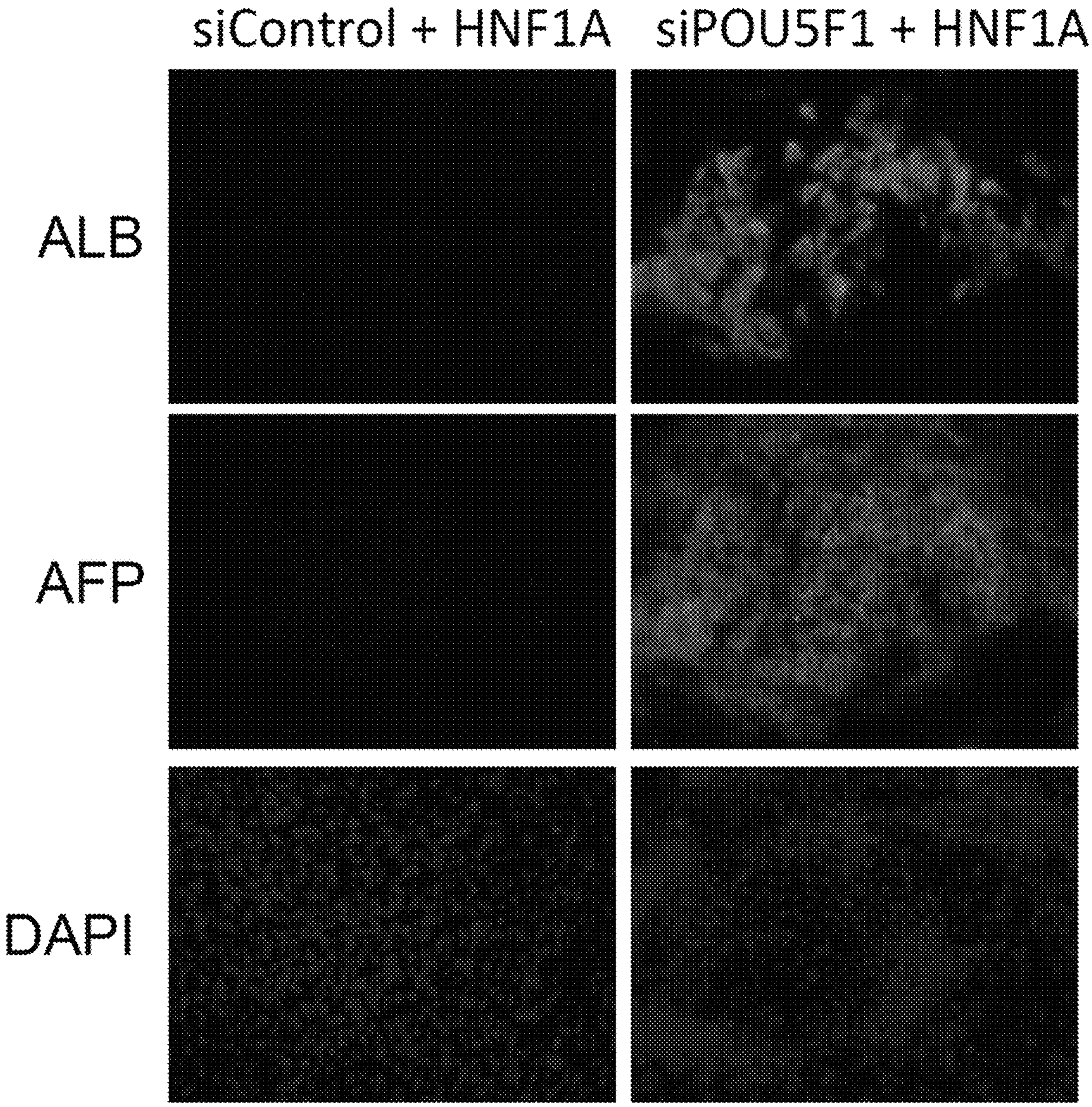
FIG. 11 Hepatocyte differentiation by siPOU5F1 and HNF1A-synRNA is shown by an immunostaining method using an albumin antibody and an AFP antibody. DAPI represents "cell nuclei".

Human ES cells were co-transfected with siControl or siPOU5F1 and synRNA for HNF1A (HNF1A-synRNA), and 1 day after that, were further transfected twice with HNF1A-synRNA. From the day after the last synRNA transfection, which was performed 2 days after the first transfection, the cells were cultured in a hepatocyte differentiation medium, and 13 days later, the cells were fixed and immunostained. While, the ES cells transfected with siControl were transfected with HNF1A-synRNA, cells expressing AFP and albumin (ALB) serving as differentiation markers for hepatocytes were hardly observed (FIG. 11). Beside, in the case of the cells co-transfected with siPOU5F1 and HNF1A-synRNA, many cells expressing albumin and AFP were observed, and thus it was confirmed that the cells were differentiated into hepatocytes (FIG. 11).

As this Example's result, it was confirmed that differentiation into desired cell types was able to be efficiently induced by introducing the transcription factors required for induction of differentiation into the desired cell types into the pluripotent stem cells in which the expression amount of the POU5F1 protein had been reduced.

Example 5

(Confirmation of Induction of Differentiation of Pluripotent Stem Cells in which Expression Amount of POU5F1 Protein has been Reduced and Demethylase is Forcibly Expressed into Desired Cell Types)

The inventors of the present invention have confirmed that pluripotent stem cells in which a demethylase is forcibly expressed allow the differentiation resistance of human pluripotent stem cells to disappear, thereby facilitating differentiation induction. A molecular mechanism by which the expression amount of the POU5F1 protein is reduced is different from a molecular mechanism by which the demethylase is forcibly expressed.

In view of the foregoing, it was confirmed whether differentiation into desired cell types was induced by introducing (adding) transcription factors required for induction of differentiation into the desired cell types to pluripotent stem cells in which the expression amount of the POU5F1 protein had been reduced and the demethylase was forcibly expressed, which were obtained by combining the reduction of the expression amount of the POU5F1 protein and the forced expression of the demethylase. The details are as described below.

Differentiation into the desired cell types was induced using synRNAs for tissue-specific transcription factors MYOD1, HNF1A, SOX9, and SPI1.

Figure 12:
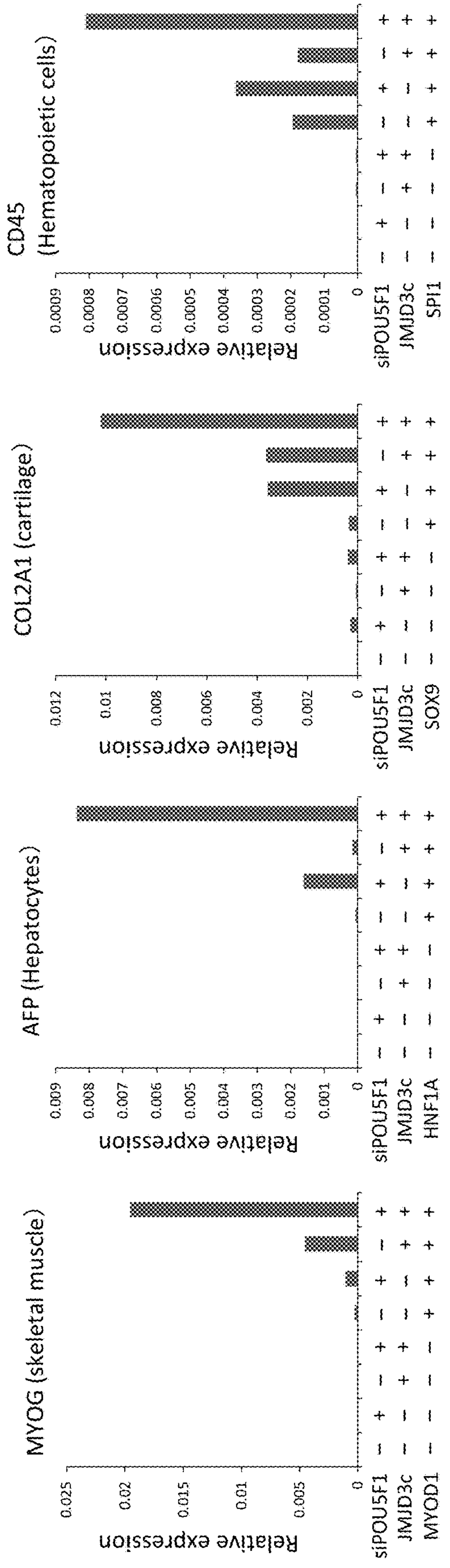
FIG. 12 It was confirmed by a real-time PCR method that differentiation induction by siPOU5F1 was further facilitated by combining forced expression of a demethylase therewith. It was confirmed that the expression of a differentiation marker gene (MYOG, AFP, COL2A, or CD45) activated by siPOU5F1 and a tissue-specific transcription factor (MYOD1, HNF1A, SOX9, or SPI1) was further upregulated by forced expression of the demethylase in a synergistic manner.

It was confirmed that the expression of differentiation marker genes MYOG (skeletal muscle), AFP (hepatocyte), COL2A1 (cartilage), CD45 (hematopoietic cell) was more increased in a synergistic manner in the case of differentiation performed by combining the reduction of the expression amount of the POU5F1 protein and the forced expression of the demethylase than in the case of differentiation performed by only one of the reduction of the expression amount of the POU5F1 protein or the forced expression of the demetylase, and the expression with synRNA (FIG. 12).

More specifically, an about 18.2-fold increase in expression of MYOG, an about 5.2-fold increase in expression of AFP, an about 2.8-fold increase in expression of COL2A1, and an about 2.2-fold increase in expression of CD45 were achieved by combining the reduction of the expression amount of the POU5F1 protein and the forced expression of the demethylase as compared to the case in which the expression amount of the POU5F1 protein was only reduced.

Further, the combination of the reduction of the expression amount of the POU5F1 protein and the forced expression of the demethylase achieved an about 4.3-fold increase in expression of MYOG, an about 54.0-fold increase in expression of AFP, an about 2.8-fold increase in expression of COL2A1, and an about 4.5-fold increase in expression of CD45 as compared to the case in which the demethylase was forcibly expressed.

In addition, in hepatocyte differentiation induction, the reduction of the expression amount of the POU5F1 protein achieved expression about 10.4 times as high as that achieved by the forced expression of the demethylase. Thus, concerning hepatocyte differentiation induction, the reduction of the expression amount of the POU5F1 protein showed a significant effect as compared to the forced expression of the demethylase.

As this Example's result, it was confirmed that the pluripotent stem cells in which the expression amount of the POU5F1 protein had been reduced and the demethylase was forcibly expressed had a synergistic differentiation induction effect (advantageous effect) as compared to the pluripotent stem cells in which the expression amount of the POU5F1 protein had been reduced and the pluripotent stem cells in which the demethylase was forcibly expressed.

Example 6

(Examples of Differentiation into Desired Cell Types Using Pluripotent Stem Cells of the Present Disclosure)

In this Example, differentiation into various desired cell types was confirmed using pluripotent stem cells in which the expression amount of the POU5F1 protein had been substantially removed or reduced on the basis of the example described as Example 3.

(Differentiation into Skeletal Muscle Cells)

During 4-day culture, human pluripotent stem cells were co-transfected with siPOU5F1 and a MYOD1 gene (SEQ ID NO: 33, SEQ ID NO: 34) once, and then transfected with the MYOD1 gene three times. It was confirmed that the cells were differentiated into skeletal muscle cells through the 4-day culture.

(Differentiation into Hepatocytes)

During 12-day culture, human pluripotent stem cells were co-transfected with siPOU5F1 and a HNF1A gene (SEQ ID NO: 35, SEQ ID NO: 36) once, and then transfected with the HNF1A gene twice. It was confirmed that the cells were differentiated into hepatocytes through the 12-day culture.

(Differentiation into Neurons)

During 5-day culture, human pluripotent stem cells are transfected with siPOU5F1 once, and then transfected with a NEUROG1 gene (SEQ ID NO: 37, SEQ ID NO: 38), a NEUROG2 gene (SEQ ID NO: 39, SEQ ID NO: 40), a NEUROG3 gene (SEQ ID NO: 41, SEQ ID NO: 42), a NEUROD1 gene (SEQ ID NO: 43, SEQ ID NO: 44), and a NEUROD2 gene (SEQ ID NO: 45, SEQ ID NO: 46) three times. The cells can be differentiated into neurons through the 5-day culture.

Example 7

(Examples of Differentiation into Desired Cell Types Using Pluripotent Stem Cells of the Present Disclosure by Use of Sendai Virus Vector)

In this Example, unlike Example 3, differentiation into various desired cell types is confirmed using pluripotent stem cells in which the expression amount of the POU5F1 protein has been substantially removed or reduced, through use of a Sendai virus vector instead of synthetic modified mRNA.

(Differentiation into Skeletal Muscle Cells)

A Sendai virus vector known per se (which is active at 33° C. and is inactivated at 37° C.) into which a transcription factor MYOD1 gene (SEQ ID NO: 33, SEQ ID NO: 34) has been cloned is used.

A suspension of human ES cells or iPS cells is infected with the Sendai virus vector at a multiplicity of infection (MOI) of 1 to 100 (25). After that, the cells are transferred to a culture plate, and the cells are cultured in a $CO_2$ incubator kept at 33° C. for 3 days. After that, the cells are transferred to a $CO_2$ incubator at 37° C., and culture is continued. As a result, skeletal muscle cells can be observed as differentiated cells.

(Differentiation into Hepatocytes)

A Sendai virus vector known per se into which a transcription factor HNF1A gene (SEQ ID NO: 35, SEQ ID NO: 36) has been cloned is used.

A suspension of human ES cells or iPS cells is infected with the Sendai virus vector at a MOI of 1 to 100 (25). After that, the cells are transferred to a culture plate, and the cells are cultured in a $CO_2$ incubator kept at 33° C. for 3 days. After that, the cells are transferred to a $CO_2$ incubator at 37° C., and culture is continued. As a result, hepatocytes can be observed as differentiated cells.

(Differentiation into Neurons)

A Sendai virus vector known per se into which a transcription factor NEUROG3 gene (SEQ ID NO: 41, SEQ ID NO: 42) has been cloned is used.

A suspension of human ES cells or iPS cells is infected with the Sendai virus vector at a MOI of 1 to 100 (25). After that, the cells are transferred to a culture plate, and the cells are cultured in a $CO_2$ incubator kept at 33° C. for 3 days. After that, the cells are transferred to a $CO_2$ incubator at 37° C., and culture is continued. As a result, neurons (motor neurons) can be observed as differentiated cells.

CONCLUSION

The inventors of the present invention have confirmed by the above-mentioned Examples that the method of differentiating a pluripotent stem cell into a desired cell type with high efficiency and the differentiation induction kit for differentiating a pluripotent stem cell into a desired cell type with high efficiency of the present invention each have at least any one of the following effects.

(1) The period of time required for cell differentiation starting with the pluripotent stem cell is shortened and/or the differentiation induction efficiency is improved.

(2) As modified synthetic mRNA for a gene is used to introduce the gene into the pluripotent stem cell, the introduced gene is not incorporated into the genome of the pluripotent stem cell, with the result that there is no risk of canceration or the like after cell differentiation induction.

(3) In the introduction of the gene into the pluripotent stem cell using the modified synthetic mRNA, the timing and number of times of the addition of the mRNA for the gene can be easily changed, and hence optimal conditions specific to each of various desired cell types can be selected so as to differentiate the pluripotent stem cell into the desired cell types.

(4) A method of reducing undifferentiated state maintenance of a pluripotent stem cell and a method of reducing differentiation resistance thereof are combined with each other to shorten the period of time required for cell differentiation starting with the pluripotent stem cell and to improve the differentiation induction efficiency in a synergistic manner.

INDUSTRIAL APPLICABILITY

According to the present invention, the novel method of differentiating a pluripotent stem cell into a desired cell type with high efficiency can be provided.

The invention claimed is:

1. A method of differentiating a pluripotent stem cell into a desired cell type, comprising any one of the following steps (1) to (2):

(1) a step of adding an siRNA, shRNA, or antisense RNA having an action of substantially removing or reducing an expression amount of a POU5F1 protein, a demethylase gene, and a modified mRNA encoding a transcription factor required for induction of differentiation into the desired cell type to a pluripotent stem cell; and (2) a step of adding a modified mRNA encoding a transcription factor required for induction of differentiation into the desired cell type and an siRNA, shRNA, or antisense RNA having an action of substantially removing or reducing an expression amount of a POU5F1 protein to a pluripotent stem cell which has a histone in which H3K27me3 modification has been substantially removed or reduced, wherein the differentiation method is of the pluripotent stem cell into a hematopoietic cell, and the transcription factor of each of the steps (1) to (2) comprises SPI1, and the removing or reducing of the expression amount of the POU5F1 protein of each of the steps (1) to (2), and production of SPI1 protein of each of the steps (1) to (2) lead to the differentiation of the pluripotent stem cell and expression of markers of hematopoietic cell differentiation.

2. The differentiation method according to claim 1, wherein the pluripotent stem cell is co-transfected with siPOU5F1 and synRNA for SPI1.

* * * * *

SEQUENCE LISTING

```
Sequence total quantity: 46
SEQ ID NO: 1            moltype = AA  length = 360
FEATURE                 Location/Qualifiers
source                  1..360
                        mol_type = protein
                        organism = Homo sapiens
SEQUENCE: 1
MAGHLASDFA FSPPPGGGGD GPGGPEPGWV DPRTWLSFQG PPGGPGIGPG VGPGSEVWGI  60
PPCPPPYEFC GGMAYCGPQV GVGLVPQGGL ETSQPEGEAG VGVESNSDGA SPEPCTVTPG  120
AVKLEKEKLE QNPEESQDIK ALQKELEQFA KLLKQKRITL GYTQADVGLT LGVLFGKVFS  180
QTTICRFEAL QLSFKNMCKL RPLLQKWVEE ADNNENLQEI CKAETLVQAR KRKRTSIENR  240
VRGNLENLFL QCPKPTLQQI SHIAQQLGLE KDVVRVWFCN RRQKGKRSSS DYAQREDFEA  300
AGSPFSGGPV SFPLAPGPHF GTPGYGSPHF TALYSSVPFP EGEAFPPVSV TTLGSPMHSN  360

SEQ ID NO: 2            moltype = DNA  length = 1083
FEATURE                 Location/Qualifiers
source                  1..1083
                        mol_type = genomic DNA
                        organism = Homo sapiens
SEQUENCE: 2
atggcgggac acctggcttc ggatttcgcc ttctcgcccc ctccaggtgg tggaggtgat  60
gggccagggg ggccggagcc gggctgggtt gatcctcgga cctggctaag cttccaaggc  120
cctcctggag ggccaggaat cgggccgggg gttgggccag gctctgaggt gtgggggatt  180
cccccatgcc ccccgccgta tgagttctgt ggggggatgg cgtactgtgg gccccaggtt  240
ggagtggggc tagtgcccca aggcggcttg gagacctctc agcctgaggg cgaagcagga  300
gtcggggtgg agagcaactc cgatggggcc tccccggagc cctgcaccgt cacccctggt  360
gccgtgaagc tggagaagga gaagctggag caaaacccgg aggagtccca ggacatcaaa  420
gctctgcaga aagaactcga gcaatttgcc aagctcctga agcagaagag gatcaccctg  480
ggatatacac aggccgatgt ggggctcacc ctgggggttc tatttgggaa ggtattcagc  540
caaacgacca tctgccgctt tgaggctctg cagcttagct tcaagaacat gtgtaagctg  600
cggcccttgc tgcagaagtg ggtggaggaa gctgacaaca atgaaaatct tcaggagata  660
tgcaaagcag aaaccctcgt gcaggcccga aagagaaagc gaaccagtat cgagaaccga  720
gtgagaggca acctggagaa tttgttcctg cagtgcccga aacccacact gcagcagatc  780
agccacatcg cccagcagct tgggctcgag aaggatgtgg tccgagtgtg gttctgtaac  840
cggcgccaga agggcaagcg atcaagcagc gactatgcac aacgagagga ttttgaggct  900
gctgggtctc ctttctcagg gggaccagtg tcctttcctc tggccccagg gccccatttt  960
ggtaccccag gctatgggag ccctcacttc actgcactgt actcctcggt ccctttccct  1020
gagggggaag cctttccccc tgtctccgtc accactctgg gctctcccat gcattcaaac  1080
tga                                                                1083

SEQ ID NO: 3            moltype = AA  length = 1682
FEATURE                 Location/Qualifiers
source                  1..1682
                        mol_type = protein
                        organism = Homo sapiens
SEQUENCE: 3
MHRAVDPPGA RAAREAFALG GLSCAGAWSS CPPHPPPRSA WLPGGRCSAS IGQPPLPAPL  60
PPSHGSSSGH PSKPYYAPGA PTPRPLHGKL ESLHGCVQAL LREPAQPGLW EQLGQLYESE  120
HDSEEATRCY HSALRYGGSF AELGPRIGRL QQAQLWNFHT GSCQHRAKVL PPLEQVWNLL  180
HLEHKRNYGA KRGGPPVKRA AEPPVVQPVP PAALSGPSGE EGLSPGGKRR RGCNSEQTGL  240
PPGLPLPPPP LPPPPPPPPP PPPPLPGLAT SPPFQLTKPG LWSTLHGDAW GPERKGSAPP  300
ERQEQRHSLP HPYPYPAPAY TAHPPGHRLV PAAPPGPGPR PPGAESHGCL PATRPPGSDL  360
RESRVQRSRM DSSVSPAATT ACVPYAPSRP PGLPGTTTSS SSSSSSNTGL RGVEPNPGIP  420
GADHYQTPAL EVSHHGRLGP SAHSSRKPFL GAPAATPHLS LPPGPSSPPP PPCPRLLRPP  480
PPPAWLKGPA CRAAREDGEI LEELFFGTEG PPRPAPPPLP HREGFLGPPA SRFSVGTQDS  540
HTPPTPPTPT TSSSNSNSGS HSSSPAGPVS FPPPPYLARS IDPLPRPPSP AQNPQDPPLV  600
PLTLALPPAP PSSCHQNTSG SFRRPESPRP RVSFPKTPEV GPGPPPGPLS KAPQPVPPGV  660
GELPARGPRL FDFPPTPLED QFEEPAEFKI LPDGLANIMK MLDESIRKEE EQQQHEAGVA  720
PQPPLKEPFA SLQSPFPTDT APTTTAPAVA VTTTTTTTTT TTATQEEEKK PPPALPPPPP  780
LAKFPPPSQP QPPPPPPPSP ASLLKSLASV LEGQKYCYRG TGAAVSTRPG PLPTTQYSPG  840
PPSGATALPP TSAAPSAQGS PQPSASSSSQ FSTSGGPWAR ERRAGEEPVP GPMTPTQPPP  900
PLSLPPARSE SEVLEEISRA CETLVERVGR SATDPADPVD TAEPADSGTE RLLPPAQAKE  960
EAGGVAAVSG SCKRRQKEHQ KEHRRHRRAC KDSVGRRPRE GRAKAKAKVP KEKSRRVLGN  1020
LDLQSEEIQG REKSRPDLGG ASKAKPPTAP APPSAPAPSA QPTPPSASVP GKKAREEAPG  1080
PPGVSRADML KLRSLSEGPP KELKIRLIKV ESGDKETFIA SEVEERRLRM ADLTISHCAA  1140
```

```
DVVRASRNAK VKGKFRESYL SPAQSVKPKI NTEEKLPREK LNPPTPSIYL ESKRDAFSPV  1200
LLQFCTDPRN PITVIRGLAG SLRLNLGLFS TKTLVEASGE HTVEVRTQVQ QPSDENWDLT  1260
GTRQIWPCES SRSHTTIAKY AQYQASSFQE SLQEEKESED EESEEPDSTT GTPPSSAPDP  1320
KNHHIIKFGT NIDLSDAKRW KPQLQELLKL PAFMRVTSTG NMLSHVGHTI LGMNTVQLYM  1380
KVPGSRTPGH QENNNFCSVN INIGPGDCEW FAVHEHYWET ISAFCDRHGV DYLTGSWWPI  1440
LDDLYASNIP VYRFVQRPGD LVWINAGTVH WVQATGWCNN IAWNVGPLTA YQYQLALERY  1500
EWNEVKNVKS IVPMIHVSWN VARTVKISDP DLFKMIKFCL LQSMKHCQVQ RESLVRAGKK  1560
IAYQGRVKDE PAYYCNECDV EVFNILFVTS ENGSRNTYLV HCEGCARRRS AGLQGVVVLE  1620
QYRTEELAQA YDAFTLVRAR RARGQRRRAL GQAAGTGFGS PAAPFPEPPP AFSPQAPAST  1680
SR                                                                1682

SEQ ID NO: 4            moltype = AA  length = 659
FEATURE                 Location/Qualifiers
source                  1..659
                        mol_type = protein
                        organism = Homo sapiens
SEQUENCE: 4
QSEEIQGREK SRPDLGGASK AKPPTAPAPP SAPAPSAQPT PPSASVPGKK AREEAPGPPG  60
VSRADMLKLR SLSEGPPKEL KIRLIKVESG DKETFIASEV EERRLRMADL TISHCAADVV  120
RASRNAKVKG KFRESYLSPA QSVKPKINTE EKLPREKLNP PTPSIYLESK RDAFSPVLLQ  180
FCTDPRNPIT VIRGLAGSLR LNLGLFSTKT LVEASGEHTV EVRTQVQQPS DENWDLTGTR  240
QIWPCESSRS HTTIAKYAQY QASSFQESLQ EEKESEDEES EEPDSTTGTP PSSAPDPKNH  300
HIIKFGTNID LSDAKRWKPQ LQELLKLPAF MRVTSTGNML SHVGHTILGM NTVQLYMKVP  360
GSRTPGHQEN NNFCSVNINI GPGDCEWFAV HEHYWETISA FCDRHGVDYL TGSWWPILDD  420
LYASNIPVYR FVQRPGDLVW INAGTVHWVQ ATGWCNNIAW NVGPLTAYQY QLALERYEWN  480
EVKNVKSIVP MIHVSWNVAR TVKISDPDLF KMIKFCLLQS MKHCQVQRES LVRAGKKIAY  540
QGRVKDEPAY YCNECDVEVF NILFVTSENG SRNTYLVHCE GCARRRSAGL QGVVVLEQYR  600
TEELAQAYDA FTLVRARRAR GQRRRALGQA AGTGFGSPAA PFPEPPPAFS PQAPASTSR   659

SEQ ID NO: 5            moltype = AA  length = 109
FEATURE                 Location/Qualifiers
source                  1..109
                        mol_type = protein
                        organism = Homo sapiens
SEQUENCE: 5
QLYMKVPGSR TPGHQENNNF CSVNINIGPG DCEWFAVHEH YWETISAFCD RHGVDYLTGS  60
WWPILDDLYA SNIPVYRFVQ RPGDLVWINA GTVHWVQATG WCNNIAWNV              109

SEQ ID NO: 6            moltype = DNA  length = 5049
FEATURE                 Location/Qualifiers
source                  1..5049
                        mol_type = genomic DNA
                        organism = Homo sapiens
SEQUENCE: 6
atgcatcggg cagtggatcc tccaggggcc cgcgctgcac gggaagcctt tgcccttggg  60
ggcctgagct gtgctggggc ctggagctcc tgcccgcctc atccccctcc tcgtagcgca  120
tggctgcctg gaggcagatg ctcagccagc attgggcagc cccgcttcc tgctcccta  180
cccccttcac atggcagtag ttctgggcac cccagcaaac catattatgc tccaggggcg  240
cccactccaa gaccctcca tgggaagctg gaatccctgc atggctgtgt gcaggcattg  300
ctccgggagc cagcccagcc agggctttgg gaacagcttg ggcaactgta cgagtcagag  360
cacgatagtg aggaggccac acgctgctac cacagcgccc ttcgatacgg aggaagcttc  420
gctgagctgg ggccccgcat tggccgactg cagcaggccc agctctggaa ctttcatact  480
ggctcctgcc agcaccgagc caaggtcctg cccccactgg agcaagtgtg gaacttgcta  540
caccttgagc acaaacggaa ctatggagcc aagcggggag gtcccccggt gaagcgagct  600
gctgaacccc cagtggtgca gcctgtgcct cctgcagcac tctcaggccc ctcaggggag  660
gagggcctca gccctggagg caagcgaagg agaggctgca actctgaaca gactggcctt  720
cccccagggc tgccactgcc tccaccacca ttaccaccac caccaccacc accaccacca  780
ccaccaccac ccctgcctgg cctggctacc agcccccat ttcagctaac caagccaggg  840
ctgtggagta ccctgcatgg agatgcctgg ggcccagagc gcaagggttc agcaccccca  900
gagcgccagg agcagcggca ctcgctgcct cacccatatc catacccagc tccagcgtac  960
accgcgcacc cccctggcca ccggctggtc ccggctgctc cccaggccc aggcccccgc  1020
cccccaggag cagagagcca tggctgcctg cctgccaccc gtccccccgg aagtgacctt  1080
agagagagca gagttcagag gtcgcggatg gactccagcg tttcaccagc agcaaccacc  1140
gcctgcgtgc cttacgcccc ttcccggccc cctggcctcc ccggcaccac caccagcagc  1200
agcagtagca gcagcagcaa cactggtctc cggggcgtgg agccgaaccc aggcattccc  1260
ggcgctgacc attaccaaac tcccgcgctg gaggtctctc accatggccg cctggggccc  1320
tcggcacaca gcagtcggaa accgttcttg ggggctcccg ctgccactcc ccacctatcc  1380
ctgccacctg gaccttcctc accccctcca cccccctgtc cccgcctctt acgcccccca  1440
ccacccccctg cctggttgaa gggtccggcc tgccgggcag cccgagagga tggagagatc  1500
ttagaagagc tcttctttgg gactgaggga cccccccgcc ctgcccccacc acccctcccc  1560
catcgcgagg gcttcttggg gcctccggcc tcccgctttt ctgtgggcac tcaggattct  1620
cacaccccctc ccactccccc aaccccaacc accagcagta gcaacagcaa cagtggcagc  1680
cacagcagca gccctgctgg gcctgtgtcc tttcccccac caccctatct ggccagaagt  1740
atagaccccc ttccccggcc tcccagccca gcacagaacc cccaggaccc acctcttgta  1800
cccctgactc ttgccctgcc tccagcccct ccttcctcct gccaccaaaa tacctcagga  1860
agcttcaggc gcccggagag cccccggccc agggtctcct tcccaaagac ccccgaggtg  1920
gggccggggc cacccccagg cccccctgagt aaagcccccc agcctgtgcc gcccggggtt  1980
ggggagctgc ctgcccgagg ccctcgactc tttgattttc cccccactcc gctggaggac  2040
cagtttgagg agccagccga attcaagatc ctacctgatg ggctggccaa catcatgaag  2100
```

```
atgctggacg aatccattcg caaggaagag gaacagcaac aacacgaagc aggcgtggcc  2160
ccccaacccc cgctgaagga gcccctttgca tctctgcagt ctcctttccc caccgacaca  2220
gcccccacca ctactgctcc tgctgtcgcc gtcaccacca ccaccaccac caccaccacc  2280
accacggcca cccaggaaga ggagaagaag ccaccaccag ccctaccacc accaccgcct  2340
ctagccaagt tccctccacc ctctcagcca cagccaccac cacccccacc ccccagcccg  2400
gccagcctgc tcaaatcctt ggcctccgtg ctggagggac aaaagtactg ttatcggggg  2460
actggagcag ctgtttccac ccggcctggg cccttgccca ccactcagta ttcccctggc  2520
cccccatcag gtgctaccgc cctgccgccc acctcagcgg cccctagcgc ccagggctcc  2580
ccacagccct ctgcttcctc gtcatctcag ttctctacct caggcgggcc ctgggcccgg  2640
gagcgcaggg cgggcgaaga gccagtcccg ggccccatga cccccaccca accgccccca  2700
cccctatctc tgcccctgc tcgctctgag tctgaggtgc tagaagagat cagccgggct  2760
tgcgagaccc ttgtggagcg ggtgggccgg agtgccactg acccagccga cccagtggac  2820
acagcagagc cagcggacag tgggactgag cgactgctgc cccccgcaca ggccaaggag  2880
gaggctggcg gggtggcggc agtgtcaggc agctgtaagc ggcgacagaa ggagcatcag  2940
aaggagcatc ggcggcacag gcgggcctgt aaggacagtg tgggtcgtcg gccccgtgag  3000
ggcagggcaa aggccaaggc caaggtcccc aaagaaaaga gccgccgggt gctggggaac  3060
ctggacctgc agagcgagga gatccagggt cgtgagaagt cccggcccga tcttggcggg  3120
gcctccaagg ccaagccacc cacagctcca gcccctccat cagctcctgc accttctgcc  3180
cagcccacac cccgtcagc ctctgtccct ggaaagaagg ctcgggagga agccccaggg  3240
ccaccgggtg tcagccgggc cgacatgctg aagctgcgct cacttagtga ggggcccccc  3300
aaggagctga agatccggct catcaaggta gagagtggtg acaaggagac ctttatcgcc  3360
tctgaggtgg aagagcggcg gctgcgcatg gcagacctca ccatcagcca ctgtgctgct  3420
gacgtcgtgc gcgccagcag gaatgccaag gtgaaaggga agtttcgaga gtcctacctt  3480
tcccctgccc agtctgtgaa accgaagatc aacactgagg agaagctgcc ccgggaaaaa  3540
ctcaaccccc ctacacccag catctatctg gagagcaaac gggatgcctt ctcacctgtc  3600
ctgctgcagt tctgtacaga ccctcgaaat cccatcacag tgatccgggg cctggcgggc  3660
tccctgcggc tcaacttggg cctcttctcc accaagaccc tggtggaagc gagtggcgaa  3720
cacaccgtgg aagttcgcac ccaggtgcag cagccctcag atgagaactg ggatctgaca  3780
ggcactcggc agatctggcc ttgtgagagc tcccgttccc acaccaccat tgccaagtac  3840
gcacagtacc aggcctcatc cttccaggag tctctgcagg aggagaagga gagtgaggat  3900
gaggagtcag aggagccaga cagcaccact ggaacccctc ctagcagcgc accagacccg  3960
aagaaccatc acatcatcaa gtttggcacc aacatcgact tgtctgatgc taagcggtgg  4020
aagccccagc tgcaggagct gctgaagctg cccgccttca tgcgggtaac atccacgggc  4080
aacatgctga gccacgtggg ccacaccatc ctgggcatga acacggtgca gctgtacatg  4140
aaggtgcccg gcagccgaac gccaggccac caggagaata acaacttctg ctccgtcaac  4200
atcaacattg gcccaggcga ctgcgagtgg ttcgcggtgc acgagcacta ctgggagacc  4260
atcagcgctt tctgtgatcg gcacggcgtg gactacttga cgggttcctg gtggccaatc  4320
ctggatgatc tctatgcatc caatattcct gtgtaccgct tcgtgcagcg acccggagac  4380
ctcgtgtgga ttaatgcggg gactgtgcac tgggtgcagg ccaccggctg gtgcaacaac  4440
attgcctgga acgtggggcc cctcaccgcc tatcagtacc agctggccct ggaacgatac  4500
gagtggaatg aggtgaagaa cgtcaaatcc atcgtgccca tgattcacgt gtcatggaac  4560
gtggctcgca cggtcaaaat cagcgacccc gacttgttca agatgatcaa gttctgcctg  4620
ctgcagtcca tgaagcactg ccaggtgcaa cgcgagagcc tggtgcgggc agggaagaaa  4680
atcgcttacc agggccgtgt caaggacgag ccagcctact actgcaacga gtgcgatgtg  4740
gaggtgttta acatcctgtt cgtgacaagt gagaatggca gccgcaacac gtacctggta  4800
cactgcgagg gctgtgcccg gcgccgcagc gcaggcctgc agggcgtggt ggtgctggag  4860
cagtaccgca ctgaggagct ggctcaggcc tacgacgcct tcacgctggt gagggcccgg  4920
cgggcgcgcg ggcagcggag gagggcactg gggcaggctg cagggacggg cttcgggagc  4980
ccggccgcgc ctttccctga gcccccgccg gctttctccc cccaggcccc agccagcacg  5040
tcgcgatga                                                         5049

SEQ ID NO: 7           moltype = DNA  length = 1980
FEATURE                Location/Qualifiers
source                 1..1980
                       mol_type = genomic DNA
                       organism = Homo sapiens
SEQUENCE: 7
cagagcgagg agatccaggg tcgtgagaag tcccggcccg atcttggcgg ggcctccaag  60
gccaagccac ccacagctcc agcccctcca tcagctcctg caccttctgc ccagcccaca  120
ccccgtcag cctctgtccc tggaaagaag gctcgggagg aagccccagg gccaccgggt  180
gtcagccggg ccgacatgct gaagctgcgc tcacttagtg aggggccccc caaggagctg  240
aagatccggc tcatcaaggt agagagtggt gacaaggaga cctttatcgc ctctgaggtg  300
gaagagcggc ggctgcgcat ggcagacctc accatcagcc actgtgctgc tgacgtcgtg  360
cgcgccagca ggaatgccaa ggtgaaaggg aagtttcgag agtcctacct ttcccctgcc  420
cagtctgtga aaccgaagat caacactgag gagaagctgc cccgggaaaa actcaacccc  480
cctacaccca gcatctatct ggagagcaaa cgggatgcct tctcacctgt cctgctgcag  540
ttctgtacag accctcgaaa tcccatcaca gtgatccggg gcctggcggg ctccctgcgg  600
ctcaacttgg gcctcttctc caccaagacc ctggtggaag cgagtggcga acacaccgtg  660
gaagttcgca cccaggtgca gcagccctca gatgagaact gggatctgac aggcactcgg  720
cagatctggc cttgtgagag ctcccgttcc cacaccacca ttgccaagta cgcacagtac  780
caggcctcat ccttccagga gtctctgcag gaggagaagg agagtgagga tgaggagtca  840
gaggagccag acagcaccac tggaacccct cctagcagcg caccagaccc gaagaaccat  900
cacatcatca agtttggcac caacatcgac ttgtctgatg ctaagcggtg gaagccccag  960
ctgcaggagc tgctgaagct gcccgccttc atgcgggtaa catccacggg caacatgctg  1020
agccacgtgg gccacaccat cctgggcatg aacacggtgc agctgtacat gaaggtgccc  1080
ggcagccgaa cgccaggcca ccaggagaat aacaacttct gctccgtcaa catcaacatt  1140
ggcccaggcg actgcgagtg gttcgcggtg cacgagcact actgggagac catcagcgct  1200
ttctgtgatc ggcacggcgt ggactacttg acgggttcct ggtggccaat cctggatgat  1260
ctctatgcat ccaatattcc tgtgtaccgc ttcgtgcagc gacccggaga cctcgtgtgg  1320
```

-continued

```
attaatgcgg ggactgtgca ctgggtgcag gccaccggct ggtgcaacaa cattgcctgg  1380
aacgtggggc ccctcaccgc ctatcagtac cagctggccc tggaacgata cgagtggaat  1440
gaggtgaaga acgtcaaatc catcgtgccc atgattcacg tgtcatggaa cgtggctcgc  1500
acggtcaaaa tcagcgaccc cgacttgttc aagatgatca agttctgcct gctgcagtcc  1560
atgaagcact gccaggtgca acgcgagagc ctggtgcggg cagggaagaa aatcgcttac  1620
cagggccgtg tcaaggacga gccagcctac tactgcaacg agtgcgatgt ggaggtgttt  1680
aacatcctgt tcgtgacaag tgagaatggc agccgcaaca cgtacctggt acactgcgag  1740
ggctgtgccc ggcgccgcag cgcaggcctg cagggcgtgg tggtgctgga gcagtaccgc  1800
actgaggagc tggctcaggc ctacgacgcc ttcacgctgg tgagggcccg gcgggcgcgc  1860
gggcagcgga ggagggcact ggggcaggct gcagggacgg gcttcgggag cccggccgcg  1920
cctttccctg agcccccgcc ggctttctcc ccccaggccc cagccagcac gtcgcgatga  1980

SEQ ID NO: 8            moltype = DNA  length = 327
FEATURE                 Location/Qualifiers
source                  1..327
                        mol_type = genomic DNA
                        organism = Homo sapiens
SEQUENCE: 8
cagctgtaca tgaaggtgcc cggcagccga acgccaggcc accaggagaa taacaacttc  60
tgctccgtca acatcaacat tggcccaggc gactgcgagt ggttcgcggt gcacgagcac  120
tactgggaga ccatcagcgc tttctgtgat cggcacggcg tggactactt gacgggttcc  180
tggtggccaa tcctggatga tctctatgca tccaatattc ctgtgtaccg cttcgtgcag  240
cgacccggag acctcgtgtg gattaatgcg gggactgtgc actgggtgca ggccaccggc  300
tggtgcaaca acattgcctg gaacgtg                                     327

SEQ ID NO: 9            moltype = AA  length = 12
FEATURE                 Location/Qualifiers
source                  1..12
                        mol_type = protein
                        organism = Human immunodeficiency virus
SEQUENCE: 9
GRKKRRQRRR PQ                                                     12

SEQ ID NO: 10           moltype = AA  length = 8
FEATURE                 Location/Qualifiers
REGION                  1..8
                        note = r8
source                  1..8
                        mol_type = protein
                        organism = synthetic construct
SEQUENCE: 10
RRRRRRRR                                                          8

SEQ ID NO: 11           moltype = AA  length = 21
FEATURE                 Location/Qualifiers
REGION                  1..21
                        note = MPG-8 (The first amino acid "Ala" is modified into
                         "bAla.")
source                  1..21
                        mol_type = protein
                        organism = synthetic construct
SEQUENCE: 11
AFLGWLGAWG TMGWSPKKKR K                                           21

SEQ ID NO: 12           moltype = DNA  length = 21
FEATURE                 Location/Qualifiers
misc_feature            1..21
                        note = sense strand of siRNA against POU5F1
source                  1..21
                        mol_type = other DNA
                        organism = synthetic construct
SEQUENCE: 12
gcccgaaaga gaaagcgaat t                                           21

SEQ ID NO: 13           moltype = DNA  length = 21
FEATURE                 Location/Qualifiers
misc_feature            1..21
                        note = antisense strand of siRNA against POU5F1
source                  1..21
                        mol_type = other DNA
                        organism = synthetic construct
SEQUENCE: 13
ttcgctttct ctttcgggcc t                                           21

SEQ ID NO: 14           moltype = DNA  length = 20
FEATURE                 Location/Qualifiers
misc_feature            1..20
                        note = qRT-PCR forward primer for MYOG
```

```
source                  1..20
                        mol_type = other DNA
                        organism = synthetic construct
SEQUENCE: 14
gccagactat cccctteetc                                       20

SEQ ID NO: 15           moltype = DNA  length = 20
FEATURE                 Location/Qualifiers
misc_feature            1..20
                        note = qRT-PCR reverse primer for MYOG
source                  1..20
                        mol_type = other DNA
                        organism = synthetic construct
SEQUENCE: 15
gaggccgcgt tatgataaaa                                       20

SEQ ID NO: 16           moltype = DNA  length = 18
FEATURE                 Location/Qualifiers
misc_feature            1..18
                        note = qRT-PCR forward primer for AFP
source                  1..18
                        mol_type = other DNA
                        organism = synthetic construct
SEQUENCE: 16
tgggacccga actttcca                                         18

SEQ ID NO: 17           moltype = DNA  length = 22
FEATURE                 Location/Qualifiers
misc_feature            1..22
                        note = qRT-PCR reverse primer for AFP
source                  1..22
                        mol_type = other DNA
                        organism = synthetic construct
SEQUENCE: 17
ggccacatcc aggactagtt tc                                    22

SEQ ID NO: 18           moltype = DNA  length = 20
FEATURE                 Location/Qualifiers
misc_feature            1..20
                        note = qRT-PCR forward primer for COL1A1
source                  1..20
                        mol_type = other DNA
                        organism = synthetic construct
SEQUENCE: 18
cctggatgcc atcaaagtct                                       20

SEQ ID NO: 19           moltype = DNA  length = 20
FEATURE                 Location/Qualifiers
misc_feature            1..20
                        note = qRT-PCR reverse primer for COL1A1
source                  1..20
                        mol_type = other DNA
                        organism = synthetic construct
SEQUENCE: 19
tcttgtcctt ggggttcttg                                       20

SEQ ID NO: 20           moltype = DNA  length = 20
FEATURE                 Location/Qualifiers
misc_feature            1..20
                        note = qRT-PCR forward primer for COL2A1
source                  1..20
                        mol_type = other DNA
                        organism = synthetic construct
SEQUENCE: 20
tttcccaggt caagatggtc                                       20

SEQ ID NO: 21           moltype = DNA  length = 20
FEATURE                 Location/Qualifiers
misc_feature            1..20
                        note = qRT-PCR reverse primer for COL2A1
source                  1..20
                        mol_type = other DNA
                        organism = synthetic construct
SEQUENCE: 21
cttcagcacc tgtctcacca                                       20

SEQ ID NO: 22           moltype = DNA  length = 20
FEATURE                 Location/Qualifiers
```

-continued

```
misc_feature          1..20
                      note = qRT-PCR forward primer for CD45
source                1..20
                      mol_type = other DNA
                      organism = synthetic construct
SEQUENCE: 22
tcctggactc ccaaaatctg                                              20

SEQ ID NO: 23         moltype = DNA  length = 20
FEATURE               Location/Qualifiers
misc_feature          1..20
                      note = qRT-PCR reverse primer for CD45
source                1..20
                      mol_type = other DNA
                      organism = synthetic construct
SEQUENCE: 23
accttgaacc cgaacatgag                                              20

SEQ ID NO: 24         moltype = DNA  length = 23
FEATURE               Location/Qualifiers
misc_feature          1..23
                      note = qRT-PCR forward primer for NESTIN
source                1..23
                      mol_type = other DNA
                      organism = synthetic construct
SEQUENCE: 24
tggttttcca gagtcttcag tga                                          23

SEQ ID NO: 25         moltype = DNA  length = 21
FEATURE               Location/Qualifiers
misc_feature          1..21
                      note = qRT-PCR reverse primer for NESTIN
source                1..21
                      mol_type = other DNA
                      organism = synthetic construct
SEQUENCE: 25
gaaacagcca tagagggcaa a                                            21

SEQ ID NO: 26         moltype = DNA  length = 960
FEATURE               Location/Qualifiers
source                1..960
                      mol_type = genomic DNA
                      organism = Homo sapiens
SEQUENCE: 26
atggagctac tgtcgccacc gctccgcgac gtagacctga cggcccccga cggctctctc  60
tgctcctttg ccacaacgga cgacttctat gacgacccgt gtttcgactc cccggacctg  120
cgcttcttcg aagacctgga cccgcgcctg atgcacgtgg gcgcgctcct gaaacccgaa  180
gagcactcgc acttccccgc ggcggtgcac ccggccccgg gcgcacgtga ggacgagcat  240
gtgcgcgcgc ccagcgggca ccaccaggcg ggccgctgcc tactgtgggc ctgcaaggcg  300
tgcaagcgca agaccaccaa cgccgaccgc cgcaaggccg ccaccatgcg cgagcggcgc  360
cgcctgagca aagtaaatga ggcctttgag acactcaagc gctgcacgtc gagcaatcca  420
aaccagcggt tgcccaaggt ggagatcctg cgcaacgcca tccgctatat cgagggcctg  480
caggctctgc tgcgcgacca ggacgccgcg ccccctggcg ccgcagccgc cttctatgcg  540
ccgggcccgc tgcccccggg ccgcggcggc gagcactaca gcggcgactc cgacgcgtcc  600
agcccgcgct ccaactgctc cgacggcatg atggactaca gcggcccccc gagcggcgcc  660
cggcggcgga actgctacga aggcgcctac tacaacgagg cgcccagcga acccaggccc  720
gggaagagtg cggcggtgtc gagcctagac tgcctgtcca gcatcgtgga gcgcatctcc  780
accgagagcc ctgcggcgcc cgccctcctg ctggcggacg tgccttctga gtcgcctccg  840
cgcaggcaag aggctgccgc ccccagcgag ggagagagca gcggcgaccc cacccagtca  900
ccggacgccg ccccgcagtg ccctgcgggt gcgaacccca acccgatata ccaggtgctc  960

SEQ ID NO: 27         moltype = DNA  length = 1896
FEATURE               Location/Qualifiers
source                1..1896
                      mol_type = genomic DNA
                      organism = Homo sapiens
SEQUENCE: 27
atggtttcta aactgagcca gctgcagacg gagctcctgg cggccctgct ggagtcaggg  60
ctgagcaaag aggcactgct ccaggcactg ggtgagccgg ggccctacct cctggctgga  120
gaaggccccc tggacaaggg ggagtcctgc ggcggcggtc gaggggagct ggctgagctg  180
cccaatgggc tgggggagac tcggggctcc gaggacgaga cggacgacga tggggaagac  240
ttcacgccac ccatcctcaa agagctggag aacctcagcc ctgaggaggc ggcccaccag  300
aaagccgtgg tggagaccct tctgcaggag gacccgtggc gtgtggcgaa gatggtcaag  360
tcctacctgc agcagcacaa catcccacag cgggaggtgg tcgataccac tggcctcaac  420
cagtcccacc tgtcccaaca cctcaacaag ggcactccca tgaagacgca gaagcgggcc  480
gccctgtaca cctggtacgt ccgcaagcag cgagaggtgg cgcagcagtt cacccatgca  540
gggcagggag ggctgattga agagcccaca ggtgatgagc taccaaccaa gaaggggcgg  600
aggaaccgtt tcaagtgggg cccagcatcc cagcagatcc tgttccaggc ctatgagagg  660
cagaagaacc ctagcaagga ggagcgagag acgctagtgg aggagtgcaa tagggcggaa  720
```

```
tgcatccaga gaggggtgtc cccatcacag gcacaggggc tgggctccaa cctcgtcacg  780
gaggtgcgtg tctacaactg gtttgccaac cggcgcaaag aagaagcctt ccggcacaag  840
ctggccatgg acacgtacag cgggcccccc ccagggccag gcccgggacc tgcgctgccc  900
gctcacagct cccctggcct gcctccacct gccctctccc ccagtaaggt ccacggtgtg  960
cgctatggac agcctgcgac cagtgagact gcagaagtac cctcaagcag cggcggtccc  1020
ttagtgacag tgtctacacc cctccaccaa gtgtccccca cgggcctgga gcccagccac  1080
agcctgctga gtacagaagc caagctggtc tcagcagctg gggcccccct ccccccctgtc  1140
agcaccctga cagcactgca cagcttggag cagacatccc caggcctcaa ccagcagccc  1200
cagaacctca tcatggcctc acttcctggg gtcatgacca tcgggcctgg tgagcctgcc  1260
tccctgggtc ctacgttcac caacacaggt gcctccaccc tggtcatcgg cctggcctcc  1320
acgcaggcac agagtgtgcc ggtcatcaac agcatgggca gcagcctgac caccctgcag  1380
cccgtccagt tctcccagcc gctgcacccc tcctaccagc agccgctcat gccacctgtg  1440
cagagccatg tgacccagag ccccttcatg gccaccatgg ctcagctgca gagcccccac  1500
gccctctaca gccacaagcc cgaggtggcc cagtacaccc acacaggcct gctcccgcag  1560
actatgctca tcaccgacac caccaacctg agcgccctgg ccagcctcac gcccaccaag  1620
caggtcttca cctcagacac tgaggcctcc agtgagtccg ggcttcacac gccggcatct  1680
caggccacca ccctccacgt ccccagccag gaccctgccg gcatccagca cctgcagccg  1740
gcccaccggc tcagcgccag ccccacagtg tcctccagca gcctggtgct gtaccagagc  1800
tcagactcca gcaatggcca gagccacctg ctgccatcca accacagcgt catcgagacc  1860
ttcatctcca cccagatggc ctcttcctcc cagttg                            1896

SEQ ID NO: 28          moltype = DNA  length = 1521
FEATURE                Location/Qualifiers
source                 1..1521
                       mol_type = genomic DNA
                       organism = Homo sapiens
SEQUENCE: 28
atgcgtattc ccgtagatcc gagcaccagc cggcgcttca gccccccctc cagcagcctg  60
cagcccggca aaatgagcga cgtgagcccg gtggtggctg cgcaacagca gcagcaacag  120
cagcagcagc aacagcagca gcagcagcag caacagcagc agcagcagca ggaggcggcg  180
gcggcggctg cggcggcggc ggcggctgcg gcggcggcag ctgcagtgcc ccggttgcgg  240
ccgcccccacg acaaccgcac catggtggag atcatcgccg accacccggc cgaactcgtc  300
cgcaccgaca gccccaactt cctgtgctcg gtgctgccct cgcactggcg ctgcaacaag  360
accctgcccg tggccttcaa ggtggtagcc ctcggagagg taccagatgg gactgtggtt  420
actgtcatgg cgggtaacga tgaaaattat tctgctgagc tccggaatgc ctctgctgtt  480
atgaaaaacc aagtagcaag gttcaacgat ctgagatttg tgggccggag tggacgaggc  540
aagagtttca ccttgaccat aaccgtcttc acaaatcctc cccaagtagc tacctatcac  600
agagcaatta aagttacagt agatggacct cgggaaccca gaaggcacag acagaagctt  660
gatgactcta aacctagttt gttctctgac cgcctcagtg atttagggcg cattcctcat  720
cccagtatga gagtaggtgt cccgcctcag aacccacggc cctccctgaa ctctgcacca  780
agtcctttta atccacaagg acagagtcag attacagacc ccaggcaggc acagtcttcc  840
ccgccgtggt cctatgacca gtcttacccc tcctacctga gccagatgac gtccccgtcc  900
atccactcta ccaccccgct gtcttccaca cggggcactg ggcttcctgc catcaccgat  960
gtgcctaggc gcatttcaga tgatgacact gccacctctg acttctgcct ctggccttcc  1020
actctcagta agaagagcca ggcaggtgct tcagaactgg gcccttttttc agaccccagg  1080
cagttcccaa gcatttcatc cctcactgag agccgcttct ccaacccacg aatgcactat  1140
ccagccacct ttacttacac cccgccagtc acctcaggca tgtccctcgg tatgtccgcc  1200
accactcact accacaccta cctgccacca ccctaccccg gctcttccca aagccagagt  1260
ggacccttcc agaccagcag cactccatat ctctactatg gcacttcgtc aggatcctat  1320
cagtttccca tggtgccggg gggagaccgg tctccttcca gaatgcttcc gccatgcacc  1380
accacctcga atggcagcac gctattaaat ccaaatttgc ctaaccagaa tgatggtgtt  1440
gacgctgatg gaagccacag cagttcccca actgttttga attctagtgg cagaatggat  1500
gaatctgttt ggcgaccata t                                            1521

SEQ ID NO: 29          moltype = DNA  length = 1527
FEATURE                Location/Qualifiers
source                 1..1527
                       mol_type = genomic DNA
                       organism = Homo sapiens
SEQUENCE: 29
atgaatctcc tggacccctt catgaagatg accgacgagc aggagaaggg cctgtccggc  60
gcccccagcc ccaccatgtc cgaggactcc gcgggctcgc cctgcccgtc gggctccggc  120
tcggacaccg agaacacgcg gccccaggag aacacgttcc ccaagggcga gcccgatctg  180
aagaaggaga gcgaggagga caagttcccc gtgtgcatcc gcgaggcggt cagccaggtg  240
ctcaaaggct acgactggac gctggtgccc atgccggtgc gcgtcaacgg ctccagcaag  300
aacaagccgc acgtcaagcg gcccatgaac gccttcatgg tgtgggcgca ggcggcgcgc  360
aggaagctcg cggaccagta cccgcacttg cacaacgccg agctcagcaa gacgctgggc  420
aagctctgga gacttctgaa cgagagcgag aagcggccct tcgtggagga ggcggagcgg  480
ctgcgcgtgc agcacaagaa ggaccacccg gattacaagt accagccgcg gcggaggaag  540
tcggtgaaga acgggcaggc ggaggcagag gaggccacgg agcagacgca catctccccc  600
aacgccatct tcaaggcgct gcaggccgac tcgccacact cctcctccgg catgagcgag  660
gtgcactccc ccggcgagca ctcggggcaa tcccagggcc caccgacccc acccaccacc  720
cccaaaaccg acgtgcagcc gggcaaggct gacctgaagc gagaggggcg cccccttgcca  780
gaggggggca gacagccccc tatcgacttc cgcgacgtgg acatcggcga gctgagcagc  840
gacgtcatct ccaacatcga gaccttcgat gtcaacgagt ttgaccagta cctgccgccc  900
aacggccacc cgggggtgcc ggccacgcac ggccaggtca cctacacggg cagctacggc  960
atcagcagca ccgcggccac cccggcgagc gcgggccacg tgtggatgtc caagcagcag  1020
gcgccgccgc cacccccgca gcagccccca caggccccgc cggcccccgca ggcgcccccg  1080
cagccgcagg cggcgccccc acagcagccg gcggcacccc cgcagcagcc acaggcgcac  1140
```

```
acgctgacca cgctgagcag cgagccgggc cagtcccagc gaacgcacat caagacggag  1200
cagctgagcc ccagccacta cagcgagcag cagcagcact cgccccaaca gatcgcctac  1260
agccccttca acctcccaca ctacagcccc tcctacccgc ccatcacccg ctcacagtac  1320
gactacaccg accaccagaa ctccagctcc tactacagcc acgcggcagg ccagggcacc  1380
ggcctctact ccaccttcac ctacatgaac cccgctcagc gccccatgta cacccccatc  1440
gccgacacct ctggggtccc ttccatcccg cagacccaca gcccccagca ctgggaacaa  1500
cccgtctaca cacagctcac tcgacct                                     1527

SEQ ID NO: 30          moltype = DNA  length = 792
FEATURE                Location/Qualifiers
source                 1..792
                       mol_type = genomic DNA
                       organism = Homo sapiens
SEQUENCE: 30
atggaagggt ttcccctcgt ccccccctcca tcagaagacc tggtgcccta tgacacggat  60
ctataccaac gccaaacgca cgagtattac ccctatctca gcagtgatgg ggagagccat  120
agcgaccatt actgggactt ccacccccac cacgtgcaca gcgagttcga gagcttcgcc  180
gagaacaact tcacggagct ccagagcgtg cagcccccgc agctgcagca gctctaccgc  240
cacatggagc tggagcagat gcacgtcctc gatacccccca tggtgccacc ccatcccagt  300
cttggccacc aggtctccta cctgccccgg atgtgcctcc agtacccatc cctgtcccca  360
gcccagccca gctcagatga ggaggagggc gagcggcaga gccccccact ggaggtgtct  420
gacggcgagg cggatggcct ggagcccggg cctgggctcc tgcctgggga gacaggcagc  480
aagaagaaga tccgcctgta ccagttcctg ttggacctgc tccgcagcgg cgacatgaag  540
gacagcatct ggtgggtgga caaggacaag ggcaccttcc agttctcgtc caagcacaag  600
gaggcgctgg cgcaccgctg gggcatccag aagggcaacc gcaagaagat gacctaccag  660
aagatggcgc gcgcgctgcg caactacggc aagacgggcg aggtcaagaa ggtgaagaag  720
aagctcacct accagttcag cggcgaagtg ctgggccgcg ggggcctggc cgagcggcgc  780
cacccgcccc ac                                                     792

SEQ ID NO: 31          moltype = DNA  length = 708
FEATURE                Location/Qualifiers
source                 1..708
                       mol_type = genomic DNA
                       organism = Homo sapiens
SEQUENCE: 31
atggaaagct ctgccaagat ggagagcggc ggcgccggcc agcagcccca gccgcagccc  60
cagcagccct tcctgccgcc cgcagcctgt ttctttgcca cggccgcagc cgcggcggcc  120
gcagccgccg cagcggcagc gcagagcgcg cagcagcagc agcagcagca gcagcagcag  180
cagcaggcgc cgcagctgag accggcggcc gacggccagc cctcaggggg cggtcacaag  240
tcagcgccca agcaagtcaa gcgacagcgc tcgtcttcgc ccgaactgat gcgctgcaaa  300
cgccggctca acttcagcgg ctttggctac agcctgccgc agcagcagcc ggccgccgtg  360
gcgcgccgca acgagcgcga gcgcaaccgc gtcaagttgg tcaacctggg ctttgccacc  420
cttcgggagc acgtccccaa cggcgcggcc aacaagaaga tgagtaaggt ggagacactg  480
cgctcggcgg tcgagtacat ccgcgcgctg cagcagctgc tggacgagca tgacgcggtg  540
agcgccgcct tccaggcagg cgtcctgtcg cccaccatct cccccaacta ctccaacgac  600
ttgaactcca tggccggctc gccggtctca tcctactcgt cggacgaggg ctcttacgac  660
ccgctcagcc ccgaggagca ggagcttctc gacttcacca actggttc              708

SEQ ID NO: 32          moltype = DNA  length = 2541
FEATURE                Location/Qualifiers
source                 1..2541
                       mol_type = genomic DNA
                       organism = Homo sapiens
SEQUENCE: 32
gggttggacc ctcgtacaga agctaatacg actcactata gggaaataag agagaaaaga  60
agagtaagaa gaaatataag agccaccccg cggtggcggc cgctctagaa ctagtggatc  120
ccccgggctg caggaattcg ataaaagcga tcgcccatca caagtttgta caaaaaagca  180
ggcttagcca ccatgtaccc atacgatgtt ccagattacg ctcctaagaa aaagaggaag  240
gtgcagagcg aggagatcca gggtcgtgag aagtcccggc ccgatcttgg cggggcctcc  300
aaggccaagc cacccacagc tccagcccct ccatcagctc ctgcaccttc tgcccagccc  360
acacccccgt cagcctctgt ccctggaaag aaggctcggg aggaagcccc agggccaccg  420
ggtgtcagcc gggccgacat gctgaagctg cgctcactta gtgaggggcc ccccaaggag  480
ctgaagatcc ggctcatcaa ggtagagagt ggtgacaagg agacctttat cgcctctgag  540
gtggaagagc ggcggctgcg catggcagac ctcaccatca gccactgtgc tgctgacgtc  600
gtgcgcgcca gcaggaatgc caaggtgaaa gggaagtttc gagagtccta cctttcccct  660
gcccagtctg tgaaaccgaa gatcaacact gaggagaagc tgccccggga aaaactcaac  720
ccccctacac ccagcatcta tctggagagc aaacgggatg ccttctcacc tgtcctgctg  780
cagttctgta cagaccctcg aaatcccatc acagtgatcc ggggcctggc gggctccctg  840
cggctcaact tgggcctctt ctccaccaag accctggtgg aagcgagtgg cgaacacacc  900
gtggaagttc gcacccaggt gcagcagccc tcagatgaga actgggatct gacaggcact  960
cggcagatct ggccttgtga gagctcccgt tcccacacca ccattgccaa gtacgcacag  1020
taccaggcct catccttcca ggagtctctg caggaggaga aggagagtga ggatgaggag  1080
tcagaggagc cagacagcac cactggaacc cctcctagca gcgcaccaga cccgaagaac  1140
catcacatca tcaagtttgg caccaacatc gacttgtctg atgctaagcg gtggaagccc  1200
cagctgcagg agctgctgaa gctgcccgcc ttcatgcggg taacatccac gggcaacatg  1260
ctgagccacg tgggccacac catcctgggc atgaacacgg tgcagctgta catgaaggtg  1320
cccggcagcc gaacgccagg ccaccaggag aataacaact tctgctccgt caacatcaac  1380
attggcccag gcgactgcga gtggttcgcg gtgcacgagc actactggga gaccatcagc  1440
gctttctgtg atcggcacgg cgtggactac ttgacgggtt cctggtggcc aatcctggat  1500
```

```
gatctctatg catccaatat tcctgtgtac cgcttcgtgc agcgacccgg agacctcgtg  1560
tggattaatg cggggactgt gcactgggtg caggccaccg gctggtgcaa caacattgcc  1620
tggaacgtgg ggcccctcac cgcctatcag taccagctgg ccctggaacg atacgagtgg  1680
aatgaggtga agaacgtcaa atccatcgtg cccatgattc acgtgtcatg gaacgtggct  1740
cgcacggtca aaatcagcga ccccgacttg ttcaagatga tcaagttctg cctgctgcag  1800
tccatgaagc actgccaggt gcaacgcgag agcctggtgc gggcagggaa gaaaatcgct  1860
taccagggcc gtgtcaagga cgagccagcc tactactgca acgagtgcga tgtggaggtg  1920
tttaacatcc tgttcgtgac aagtgagaat ggcagccgca acacgtacct ggtacactgc  1980
gagggctgtg cccggcgccg cagcgcaggc ctgcagggcg tggtggtgct ggagcagtac  2040
cgcactgagg agctggctca ggcctacgac gccttcacgc tggtgagggc ccggcgggcg  2100
cgcgggcagc ggaggagggc actggggcag gctgcaggga cgggcttcgg gagcccggcc  2160
gcgcctttcc ctgagccccc gccggctttc tccccccagg ccccagccag cacgtcgcga  2220
tgaacccagc tttcttgtac aaagtggtga tggccgctgt ttaaaacttt tatcaagctt  2280
atcgataccg tcgacctcga atgctgcctt ctgcggggct tgccttctgg ccatgccctt  2340
cttctctccc ttgcacctgt acctcttggt ctttgaataa agcctgagta ggaagtgagg  2400
gtctagaact agtgtcgacg caaaaaaaaa aaaaaaaaaa aaaaaaaaaa aaaaaaaaaa  2460
aaaaaaaaaa aaaaaaaaaa aaaaaaaaaa aaaaaaaaaa aaaaaaaaaa aaaaaaaaaa  2520
aaaaaaaaaa aaaaaaaaaa a                                            2541

SEQ ID NO: 33           moltype = DNA  length = 1574
FEATURE                 Location/Qualifiers
source                  1..1574
                        mol_type = genomic DNA
                        organism = Homo sapiens
SEQUENCE: 33
gggttggacc ctcgtacaga agctaatacg actcactata gggaaataag agagaaaaga  60
agagtaagaa gaaatataag agccaccccg cggtggcggc cgctctagaa ctagtggatc  120
ccccgggctg caggaattcg ataaaagcga tcgcccatca caagtttgta caaaaaagca  180
ggctccgcgg ccgcccctt caccgctagg gataacaggg taatagaagg agccgccacc  240
atggagctac tgtcgccacc gctccgcgac gtagacctga cggcccccga cggctctctc  300
tgctcctttg ccacaacgga cgacttctat gacgacccgt gtttcgactc cccggacctg  360
cgcttcttcg aagacctgga cccgcgcctg atgcacgtgg gcgcgctcct gaaacccgaa  420
gagcactcgc acttccccgc ggcggtgcac ccggcccgg gcgcacgtga ggacgagcat  480
gtgcgcgcgc ccagcgggca ccaccaggcg ggccgctgcc tactgtgggc ctgcaaggcg  540
tgcaagcgca agaccaccaa cgccgaccgc cgcaaggccg ccaccatgcg cgagcggcgc  600
cgcctgagca aagtaaatga ggcctttgag acactcaagc gctgcacgtc gagcaatcca  660
aaccagcggt tgcccaaggt ggagatcctg cgcaacgcca tccgctatat cgagggcctg  720
caggctctgc tgcgcgacca ggacgccgcg ccccctggcg ccgcagccgc cttctatgcg  780
ccgggcccgc tgcccccggg ccgcggcggc gagcactaca gcggcgactc cgacgcgtcc  840
agcccgcgct ccaactgctc cgacggcatg atggactaca gcggcccccc gagcggcgcc  900
cggcggcgga actgctacga aggcgcctac tacaacgagg cgcccagcga acccaggccc  960
gggaagagtg cggcggtgtc gagcctagac tgcctgtcca gcatcgtgga gcgcatctcc  1020
accgagagcc ctgcggcgcc cgccctcctg ctggcggacg tgccttctga gtcgcctccg  1080
cgcaggcaag aggctgccgc ccccagcgag ggagagagca gcggcgaccc cacccagtca  1140
ccggacgccg ccccgcagtg ccctgcgggt gcgaacccca acccgatata ccaggtgctc  1200
tgagtttcct gtgaacaatt gctcctctct taaggtagca aagggtgggc gcgccgaccc  1260
agctttcttg tacaaagtgg tgatggccgc tgtttaaaac ttttatcaag cttatcgata  1320
ccgtcgacct cgaatgctgc cttctgcggg gcttgccttc tggccatgcc cttcttctct  1380
cccttgcacc tgtacctctt ggtctttgaa taaagcctga gtaggaagtg agggtctaga  1440
actagtgtcg acgcaaaaaa aaaaaaaaaa aaaaaaaaaa aaaaaaaaaa aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaa                                                   1574

SEQ ID NO: 34           moltype = AA  length = 320
FEATURE                 Location/Qualifiers
source                  1..320
                        mol_type = protein
                        organism = Homo sapiens
SEQUENCE: 34
MELLSPPLRD VDLTAPDGSL CSFATTDDFY DDPCFDSPDL RFFEDLDPRL MHVGALLKPE  60
EHSHFPAAVH PAPGAREDEH VRAPSGHHQA GRCLLWACKA CKRKTTNADR RKAATMRERR  120
RLSKVNEAFE TLKRCTSSNP NQRLPKVEIL RNAIRYIEGL QALLRDQDAA PPGAAAAFYA  180
PGPLPPGRGG EHYSGDSDAS SPRSNCSDGM MDYSGPPSGA RRRNCYEGAY YNEAPSEPRP  240
GKSAAVSSLD CLSSIVERIS TESPAAPALL LADVPSESPP RRQEAAAPSE GESSGDPTQS  300
PDAAPQCPAG ANPNPIYQVL                                              320

SEQ ID NO: 35           moltype = DNA  length = 2414
FEATURE                 Location/Qualifiers
source                  1..2414
                        mol_type = genomic DNA
                        organism = Homo sapiens
SEQUENCE: 35
gggttggacc ctcgtacaga agctaatacg actcactata gggaaataag agagaaaaga  60
agagtaagaa gaaatataag agccaccccg cggtggcggc cgctctagaa ctagtggatc  120
ccccgggctg caggaattcg ataaaagcga tcgcccatca caagtttgta caaaaaagca  180
ggctccacca tggtttctaa actgagccag ctgcagacgg agctcctggc ggccctgctg  240
gagtcagggc tgagcaaaga ggcactgctc caggcactgg gtgagccggg gccctacctc  300
ctggctggag aaggcccccct ggacaagggg gagtcctgcg gcggcggtcg aggggagctg  360
gctgagctgc ccaatgggct gggggagact cggggctccg aggacgagac ggacgacgat  420
```

-continued

```
ggggaagact tcacgccacc catcctcaaa gagctggaga acctcagccc tgaggaggcg  480
gcccaccaga aagccgtggt ggagaccctt ctgcaggagg acccgtggcg tgtggcgaag  540
atggtcaagt cctacctgca gcagcacaac atcccacagc gggaggtggt cgataccact  600
ggcctcaacc agtcccacct gtcccaacac ctcaacaagg gcactcccat gaagacgcag  660
aagcgggccg ccctgtacac ctggtacgtc cgcaagcagc gagaggtggc gcagcagttc  720
acccatgcag ggcagggagg gctgattgaa gagcccacag gtgatgagct accaaccaag  780
aaggggcgga ggaaccgttt caagtggggc ccagcatccc agcagatcct gttccaggcc  840
tatgagaggc agaagaaccc tagcaaggag gagcgagaga cgctagtgga ggagtgcaat  900
agggcggaat gcatccagag aggggtgtcc ccatcacagg cacaggggct gggctccaac  960
ctcgtcacgg aggtgcgtgt ctacaactgg tttgccaacc ggcgcaaaga agaagccttc  1020
cggcacaagc tggccatgga cacgtacagc gggccccccc cagggccagg cccgggacct  1080
gcgctgcccg ctcacagctc ccctggcctg cctccacctg ccctctcccc cagtaaggtc  1140
cacggtgtgc gctatggaca gcctgcgacc agtgagactg cagaagtacc ctcaagcagc  1200
ggcggtccct tagtgacagt gtctacaccc ctccaccaag tgtcccccac gggcctggag  1260
cccagccaca gcctgctgag tacagaagcc aagctggtct cagcagctgg gggcccccctc  1320
ccccctgtca gcaccctgac agcactgcac agcttggagc agacatcccc aggcctcaac  1380
cagcagcccc agaacctcat catggcctca cttcctgggg tcatgaccat cgggcctggt  1440
gagcctgcct ccctgggtcc tacgttcacc aacacaggtg cctccaccct ggtcatcggc  1500
ctggcctcca cgcaggcaca gagtgtgccg gtcatcaaca gcatgggcag cagcctgacc  1560
accctgcagc ccgtccagtt ctcccagccg ctgcacccct cctaccagca gccgctcatg  1620
ccacctgtgc agagccatgt gacccagagc cccttcatgg ccaccatggc tcagctgcag  1680
agcccccacg ccctctacag ccacaagccc gaggtggccc agtacaccca cacaggcctg  1740
ctcccgcaga ctatgctcat caccgacacc accaacctga gcgccctggc cagcctcacg  1800
cccaccaagc aggtcttcac ctcagacact gaggcctcca gtgagtccgg gcttcacacg  1860
ccggcatctc aggccaccac cctccacgtc cccagccagg accctgccgg catccagcac  1920
ctgcagccgg cccaccggct cagcgccagc cccacagtgt cctccagcag cctggtgctg  1980
taccagagct cagactccag caatggccag agccacctgc tgccatccaa ccacagcgtc  2040
atcgagacct tcatctccac ccagatggcc tcttcctccc agttgtgagc ggccgcaccc  2100
agctttcttg tacaaagtgg tgatggccgc tgtttaaaac ttttatcaag cttatcgata  2160
ccgtcgacct cgaatgctgc cttctgcggg gcttgccttc tggccatgcc cttcttctct  2220
cccttgcacc tgtacctctt ggtctttgaa taaagcctga gtaggaagtg agggtctaga  2280
actagtgtcg acgcaaaaaa aaaaaaaaaa aaaaaaaaaa aaaaaaaaaa aaaaaaaaaa  2340
aaaaaaaaaa aaaaaaaaaa aaaaaaaaaa aaaaaaaaaa aaaaaaaaaa aaaaaaaaaa  2400
aaaaaaaaaa aaaa                                                    2414

SEQ ID NO: 36          moltype = AA  length = 632
FEATURE                Location/Qualifiers
source                 1..632
                       mol_type = protein
                       organism = Homo sapiens
SEQUENCE: 36
MVSKLSQLQT ELLAALLESG LSKEALLQAL GEPGPYLLAG EGPLDKGESC GGGRGELAEL  60
PNGLGETRGS EDETDDDGED FTPPILKELE NLSPEEAAHQ KAVVETLLQE DPWRVAKMVK  120
SYLQQHNIPQ REVVDTTGLN QSHLSQHLNK GTPMKTQKRA ALYTWYVRKQ REVAQQFTHA  180
GQGGLIEEPT GDELPTKKGR RNRFKWGPAS QQILFQAYER QKNPSKEERE TLVEECNRAE  240
CIQRGVSPSQ AQGLGSNLVT EVRVYNWFAN RRKEEAFRHK LAMDTYSGPP PGPGPGPALP  300
AHSSPGLPPP ALSPSKVHGV RYGQPATSET AEVPSSSGGP LVTVSTPLHQ VSPTGLEPSH  360
SLLSTEAKLV SAAGGPLPPV STLTALHSLE QTSPGLNQQP QNLIMASLPG VMTIGPGEPA  420
SLGPTFTNTG ASTLVIGLAS TQAQSVPVIN SMGSSLTTLQ PVQFSQPLHP SYQQPLMPPV  480
QSHVTQSPFM ATMAQLQSPH ALYSHKPEVA QYTHTGLLPQ TMLITDTTNL SALASLTPTK  540
QVFTSDTEAS SESGLHTPAS QATTLHVPSQ DPAGIQHLQP AHRLSASPTV SSSSLVLYQS  600
SDSSNGQSHL LPSNHSVIET FISTQMASSS QL                                632

SEQ ID NO: 37          moltype = DNA  length = 1222
FEATURE                Location/Qualifiers
source                 1..1222
                       mol_type = genomic DNA
                       organism = Homo sapiens
SEQUENCE: 37
gggttggacc ctcgtacaga agctaatacg actcactata gggaaataag agagaaaaga  60
agagtaagaa gaaatataag agccaccccg cggtggcggc cgctctagaa ctagtggatc  120
ccccgggctg caggaattcg ataaaagcga tcgcccatca caagtttgta caaaaaagca  180
ggctccacca tgccagcccg ccttgagacc tgcatctccg acctcgactg cgccagcagc  240
agcggcagtg acctatccgg cttcctcacc gacgaggaag actgtgccag actccaacag  300
gcagcctccg cttcggggcc gcccgcgccg gcccgcaggg gcgcgcccaa tatctcccgg  360
gcgtctgagg ttccaggggc acaggacgac gagcaggaga ggcggcggcg ccgcggccgg  420
acgcgggtcc gctccgaggc gctgctgcac tcgctgcgca ggagccggcg cgtcaaggcc  480
aacgatcgcg agcgcaaccg catgcacaac ttgaacgcgg ccctggacgc actgcgcagc  540
gtgctgccct cgttccccga cgacaccaag ctcaccaaaa tcgagacgct gcgcttcgcc  600
tacaactaca tctgggctct ggccgagaca ctgcgcctgg cggatcaagg gctgcccgga  660
ggcggtgccc gggagcgcct cctgccgccg cagtgcgtcc cctgcctgcc cggtccccca  720
agccccgcca gcgacgcgga gtcctggggc tcaggtgccg ccgccgcctc cccgctctct  780
gaccccagta gcccagccgc ctccgaagac ttcacctacc gccccggcga ccctgttttc  840
tccttcccaa gcctgcccaa agacttgctc cacacaacgc cctgtttcat tccttaccac  900
taggacccag ctttcttgta caaagtggtg atggccgctg tttaaaactt ttatcaagct  960
tatcgatacc gtcgacctcg aatgctgcct tctgcggggc ttgccttctg gccatgccct  1020
tcttctctcc cttgcacctg tacctcttgg tctttgaata aagcctgagt aggaagtgag  1080
```

```
ggtctagaac tagtgtcgac gcaaaaaaaa aaaaaaaaaa aaaaaaaaaa aaaaaaaaaa  1140
aaaaaaaaaa aaaaaaaaaa aaaaaaaaaa aaaaaaaaaa aaaaaaaaaa aaaaaaaaaa  1200
aaaaaaaaaa aaaaaaaaaa aa                                           1222

SEQ ID NO: 38          moltype = AA  length = 237
FEATURE                Location/Qualifiers
source                 1..237
                       mol_type = protein
                       organism = Homo sapiens
SEQUENCE: 38
MPARLETCIS DLDCASSSGS DLSGFLTDEE DCARLQQAAS ASGPPAPARR GAPNISRASE  60
VPGAQDDEQE RRRRRGRTRV RSEALLHSLR RSRRVKANDR ERNRMHNLNA ALDALRSVLP  120
SFPDDTKLTK IETLRFAYNY IWALAETLRL ADQGLPGGGA RERLLPPQCV PCLPGPPSPA  180
SDAESWGSGA AAASPLSDPS SPAASEDFTY RPGDPVFSFP SLPKDLLHTT PCFIPYH     237

SEQ ID NO: 39          moltype = DNA  length = 1357
FEATURE                Location/Qualifiers
source                 1..1357
                       mol_type = genomic DNA
                       organism = Homo sapiens
SEQUENCE: 39
gggttggacc ctcgtacaga agctaatacg actcactata gggaaataag agagaaaaga  60
agagtaagaa gaaatataag agccaccccg cggtggcggc cgctctagaa ctagtggatc  120
ccccgggctg caggaattcg ataaaagcga tcgcccatca caagtttgta caaaaaagca  180
ggctccgcgg ccgcccccctt caccatgttc gtcaaatccg agaccttgga gttgaaggag  240
gaagaggacg tgttagtgct gctcggatcg gcctcccccg ccttggcggc cctgaccccg  300
ctgtcatcca gcgccgacga agaagaggag gaggagccgg gcgcgtcagg tggggcgcgt  360
cggcagcgcg gggctgaggc cgggcagggg gcgcggggcg gcgtggctgc gggtgcggag  420
ggctgccggc ccgcacggct gctgggtctg gtacacgatt gcaaacggcg cccttcccgg  480
gcgcgggccg tctcccgagg cgccaagacg gccgagacgg tgcagcgcat caagaagacc  540
cgtagactga aggccaacaa ccgcgagcga aaccgcatgc acaacctcaa cgcggcactg  600
gacgcgctgc gcgaggtgct ccccacgttc cccgaggacg ccaagctcac caagatcgag  660
accctgcgct tcgcccacaa ctacatctgg gcactcaccg agaccctgcg cctggcggat  720
cactgcgggg gcggcggcgg gggcctgccg ggggcgctct tctccgaggc agtgttgctg  780
agcccgggag gcgccagcgc cgccctgagc agcagcggag acagcccctc gcccgcctcc  840
acgtggagtt gcaccaacag ccccgcgccg tcctcctccg tgtcctccaa ttccacctcc  900
ccctacagct gcactttatc gcccgccagc ccggccgggt cagacatgga ctattggcag  960
cccccacctc ccgacaagca ccgctatgca cctcacctcc ccatagccag ggattgtatc  1020
tagaagggtg ggcgcgccga cccagctttc ttgtacaaag tggtgatggc cgctgtttaa  1080
aacttttatc aagcttatcg ataccgtcga cctcgaatgc tgccttctgc ggggcttgcc  1140
ttctggccat gcccttcttc tctcccttgc acctgtacct cttggtcttt gaataaagcc  1200
tgagtaggaa gtgagggtct agaactagtg tcgacgcaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaa                           1357

SEQ ID NO: 40          moltype = AA  length = 272
FEATURE                Location/Qualifiers
source                 1..272
                       mol_type = protein
                       organism = Homo sapiens
SEQUENCE: 40
MFVKSETLEL KEEEDVLVLL GSASPALAAL TPLSSSADEE EEEEPGASGG ARRQRGAEAG  60
QGARGGVAAG AEGCRPARLL GLVHDCKRRP SRARAVSRGA KTAETVQRIK KTRRLKANNR  120
ERNRMHNLNA ALDALREVLP TFPEDAKLTK IETLRFAHNY IWALTETLRL ADHCGGGGGG  180
LPGALFSEAV LLSPGGASAA LSSSGDSPSP ASTWSCTNSP APSSSVSSNS TSPYSCTLSP  240
ASPAGSDMDY WQPPPPDKHR YAPHLPIARD CI                                272

SEQ ID NO: 41          moltype = DNA  length = 1153
FEATURE                Location/Qualifiers
source                 1..1153
                       mol_type = genomic DNA
                       organism = Homo sapiens
SEQUENCE: 41
gggttggacc ctcgtacaga agctaatacg actcactata gggaaataag agagaaaaga  60
agagtaagaa gaaatataag agccaccccg cggtggcggc cgctctagaa ctagtggatc  120
ccccgggctg caggaattcg ataaaagcga tcgcccatca caagtttgta caaaaaagca  180
ggcttcacca tgacgcctca accctcgggt gcgcccactg tccaagtgac ccgtgagacg  240
gagcggtcct tccccagagc ctcggaagac gaagtgacct gccccacgtc cgccccgccc  300
agccccactc gcacacgggg gaactgcgca gaggcggaag agggaggctg ccgaggggcc  360
ccgaggaagc tccgggcacg gcgcgggggga cgcagccggc ctaagagcga gttggcactg  420
agcaagcagc gacggagtcg gcgaaagaag gccaacgacc gcgagcgcaa tcgaatgcac  480
aacctcaact cggcactgga cgccctgcgc ggtgtcctgc ccaccttccc agacgacgcg  540
aagctcacca agatcgagac gctgcgcttc gcccacaact acatctgggc gctgactcaa  600
acgctgcgca tagcggacca cagcttgtac gcgctggagc cgccggcgcc gcactgcggg  660
gagctgggca gcccaggcgg ttcccccggg gactgggggt ccctctactc cccagtctcc  720
caggctggca gcctgagtcc cgccgcgtcg ctggaggagc gacccgggct gctgggggcc  780
accttttccg cctgcttgag cccaggcagt ctggctttct cagattttct gtgagaccca  840
gctttcttgt acaaagtggt gatggccgct gtttaaaact tttatcaagc ttatcgatac  900
cgtcgacctc gaatgctgcc ttctgcgggg cttgccttct ggccatgccc ttcttctctc  960
```

```
ccttgcacct gtacctcttg gtctttgaat aaagcctgag taggaagtga gggtctagaa  1020
ctagtgtcga cgcaaaaaaa aaaaaaaaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaa                                                     1153

SEQ ID NO: 42          moltype = AA  length = 214
FEATURE                Location/Qualifiers
source                 1..214
                       mol_type = protein
                       organism = Homo sapiens
SEQUENCE: 42
MTPQPSGAPT VQVTRETERS FPRASEDEVT CPTSAPPSPT RTRGNCAEAE EGGCRGAPRK  60
LRARRGGRSR PKSELALSKQ RRSRRKKAND RERNRMHNLN SALDALRGVL PTFPDDAKLT  120
KIETLRFAHN YIWALTQTLR IADHSLYALE PPAPHCGELG SPGGSPGDWG SLYSPVSQAG  180
SLSPAASLEE RPGLLGATFS ACLSPGSLAF SDFL                              214

SEQ ID NO: 43          moltype = DNA  length = 1609
FEATURE                Location/Qualifiers
source                 1..1609
                       mol_type = genomic DNA
                       organism = Homo sapiens
SEQUENCE: 43
gggttggacc ctcgtacaga agctaatacg actcactata gggaaataag agagaaaaga  60
agagtaagaa gaaatataag agccaccccg cggtggcggc cgctctagaa ctagtggatc  120
ccccgggctg caggaattcg ataaaagcga tcgcccatca caagtttgta caaaaaagca  180
ggctccgcgg ccgcccctt caccatgacc aaatcgtaca gcgagagtgg gctgatgggc  240
gagcctcagc cccaaggtcc tccaagctgg acagacgagt gtctcagttc tcaggacgag  300
gagcacgagg cagacaagaa ggaggacgac ctcgaagcca tgaacgcaga ggaggactca  360
ctgaggaacg ggggagagga ggaggacgaa gatgaggacc tggaagagga ggaagaagag  420
gaagaggagg atgacgatca aaagcccaag agacgcggcc ccaaaaagaa gaagatgact  480
aaggctcgcc tggagcgttt taaattgaga cgcatgaagg ctaacgcccg ggagcggaac  540
cgcatgcacg gactgaacgc ggcgctagac aacctgcgca aggtggtgcc ttgctattct  600
aagacgcaga agctgtccaa aatcgagact ctgcgcttgg ccaagaacta catctgggct  660
ctgtcggaga tcctgcgctc aggcaaaagc ccagacctgg tctccttcgt tcagacgctt  720
tgcaagggct tatcccaacc caccaccaac ctggttgcgg gctgcctgca actcaatcct  780
cggacttttc tgcctgagca gaaccaggac atgccccccc acctgccgac ggccagcgct  840
tccttccctg tacaccccta ctcctaccag tcgcctgggc tgcccagtcc gccttacggt  900
accatggaca gctcccatgt cttccacgtt aagcctccgc cgcacgccta cagcgcagcg  960
ctggagccct tctttgaaag ccctctgact gattgcacca gcccttcctt tgatggaccc  1020
ctcagcccgc cgctcagcat caatggcaac ttctctttca aacacgaacc gtccgccgag  1080
tttgagaaaa attatgcctt taccatgcac tatcctgcag cgacactggc aggggcccaa  1140
agccacggat caatcttctc aggcaccgct gcccctcgct gcgagatccc catagacaat  1200
attatgtcct tcgatagcca ttcacatcat gagcgagtca tgagtgccca gctcaatgcc  1260
atatttcatg attagaaggg tgggcgcgcc gacccagctt tcttgtacaa agtggtgatg  1320
gccgctgttt aaaactttta tcaagcttat cgataccgtc gacctcgaat gctgccttct  1380
gcggggcttg ccttctggcc atgcccttct tctctccctt gcacctgtac ctcttggtct  1440
ttgaataaag cctgagtagg aagtgagggt ctagaactag tgtcgacgca aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaa             1609

SEQ ID NO: 44          moltype = AA  length = 356
FEATURE                Location/Qualifiers
source                 1..356
                       mol_type = protein
                       organism = Homo sapiens
SEQUENCE: 44
MTKSYSESGL MGEPQPQGPP SWTDECLSSQ DEEHEADKKE DDLEAMNAEE DSLRNGGEEE  60
DEDEDLEEEE EEEEEDDDQK PKRRGPKKKK MTKARLERFK LRRMKANARE RNRMHGLNAA  120
LDNLRKVVPC YSKTQKLSKI ETLRLAKNYI WALSEILRSG KSPDLVSFVQ TLCKGLSQPT  180
TNLVAGCLQL NPRTFLPEQN QDMPPHLPTA SASFPVHPYS YQSPGLPSPP YGTMDSSHVF  240
HVKPPPHAYS AALEPFFESP LTDCTSPSFD GPLSPPLSIN GNFSFKHEPS AEFEKNYAFT  300
MHYPAATLAG AQSHGSIFSG TAAPRCEIPI DNIMSFDSHS HHERVMSAQL NAIFHD      356

SEQ ID NO: 45          moltype = DNA  length = 1687
FEATURE                Location/Qualifiers
source                 1..1687
                       mol_type = genomic DNA
                       organism = Homo sapiens
SEQUENCE: 45
gggttggacc ctcgtacaga agctaatacg actcactata gggaaataag agagaaaaga  60
agagtaagaa gaaatataag agccaccccg cggtggcggc cgctctagaa ctagtggatc  120
ccccgggctg caggaattcg ataaaagcga tcgcccatca caagtttgta caaaaaagca  180
ggctccgcgg ccgcccctt caccatgctg acccgcctgt tcagcgagcc cggccttctc  240
tcggacgtgc ccaagttcgc cagctggggc gacggcgaag acgacgagcc gaggagcgac  300
aagggcgacg cgccgccacc gccaccgcct gcgcccgggc caggggctcc ggggccagcc  360
cgggcggcca agccagtccc tctccgtgga gaagagggga cggaggccac gttggccgag  420
gtcaaggagg aaggcgagct ggggggagag gaggaggagg aagaggagga ggaagaagga  480
ctggacgagg cggagggcga gcggcccaag aagggcgggc ccaagaagcg caagatgacc  540
aaggcgcgct tggagcgctc caagcttcgg cggcagaagg cgaacgcgcg ggagcgcaac  600
```

-continued

```
cgcatgcacg acctgaacgc agccctggac aacctgcgca aggtggtgcc ctgctactcc  660
aagacgcaga agctgtccaa gatcgagacg ctgcgcctag ccaagaacta tatctgggcg  720
ctctcggaga tcctgcgctc cggcaagcgg ccagacctag tgtcctacgt gcagactctg  780
tgcaagggtc tgtcgcagcc caccaccaat ctggtggccg gctgtctgca gctcaactct  840
cgcaacttcc tcacggagca aggcgccgac ggtgccggcc gcttccacgg ctcgggcggc  900
ccgttcgcca tgcaccccta cccgtacccg tgctcgcgcc tggcgggcgc acagtgccag  960
gcggccggcg gcctgggcgg cggcgcggcg cacgccctgc ggacccacgg ctactgcgca  1020
gcctacgaga cgctgtatgc ggcggcaggc ggtggcggcg cgagcccgga ctacaacagc  1080
tccgagtacg agggcccgct cagccccccg ctctgtctca atggcaactt ctcactcaag  1140
caggactcct cgcccgacca cgagaaaagc taccactact ctatgcacta ctcggcgctg  1200
cccggttcgc ggcccacggg ccacgggcta gtcttcggct cgtcggctgt gcgcgggggc  1260
gtccactcgg agaatctctt gtcttacgat atgcaccttc accacgaccg gggccccatg  1320
tacgaggagc tcaatgcgtt ttttcataac tgaaagggtg ggcgcgccga cccagctttc  1380
ttgtacaaag tggtgatggc cgctgtttaa aacttttatc aagcttatcg ataccgtcga  1440
cctcgaatgc tgccttctgc ggggcttgcc ttctggccat gcccttcttc tctcccttgc  1500
acctgtacct cttggtcttt gaataaagcc tgagtaggaa gtgagggtct agaactagtg  1560
tcgacgcaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaa                                                            1687

SEQ ID NO: 46           moltype = AA  length = 382
FEATURE                 Location/Qualifiers
source                  1..382
                        mol_type = protein
                        organism = Homo sapiens
SEQUENCE: 46
MLTRLFSEPG LLSDVPKFAS WGDGEDDEPR SDKGDAPPPP PPAPGPGAPG PARAAKPVPL  60
RGEEGTEATL AEVKEEGELG GEEEEEEEEE EGLDEAEGER PKKGGPKKRK MTKARLERSK  120
LRRQKANARE RNRMHDLNAA LDNLRKVVPC YSKTQKLSKI ETLRLAKNYI WALSEILRSG  180
KRPDLVSYVQ TLCKGLSQPT TNLVAGCLQL NSRNFLTEQG ADGAGRFHGS GGPFAMHPYP  240
YPCSRLAGAQ CQAAGGLGGG AAHALRTHGY CAAYETLYAA AGGGGASPDY NSSEYEGPLS  300
PPLCLNGNFS LKQDSSPDHE KSYHYSMHYS ALPGSRPTGH GLVFGSSAVR GGVHSENLLS  360
YDMHLHHDRG PMYEELNAFF HN                                           382
```